(12) United States Patent
Akireddy et al.

(10) Patent No.: US 8,802,694 B2
(45) Date of Patent: Aug. 12, 2014

(54) 3,6-DIAZABICYCLO[3.1.1]HEPTANES AS NEURONAL NICOTINIC ACETYCHOLINE RECEPTOR LIGANDS

(75) Inventors: Srinivasa Rao Akireddy, Winston-Salem, NC (US); Balwinder Singh Bhatti, Winston-Salem, NC (US); Ronald Joseph Heemstra, Lewisville, NC (US); Srinivasa V. Murthy, Lewisville, NC (US); Jon-Paul Strachan, Burlington, NC (US); Yunde Xiao, Clemmons, NC (US)

(73) Assignee: Targacept, Inc., Winston-Salem, NC (US)

( * ) Notice: Subject to any disclaimer, the term of this patent is extended or adjusted under 35 U.S.C. 154(b) by 92 days.

(21) Appl. No.: 13/514,084

(22) PCT Filed: Dec. 3, 2010

(86) PCT No.: PCT/US2010/058836
§ 371 (c)(1),
(2), (4) Date: Aug. 15, 2012

(87) PCT Pub. No.: WO2011/071758
PCT Pub. Date: Jun. 16, 2011

(65) Prior Publication Data
US 2012/0309737 A1    Dec. 6, 2012

Related U.S. Application Data

(60) Provisional application No. 61/267,218, filed on Dec. 7, 2009.

(51) Int. Cl.
*A61K 31/439* (2006.01)
*C07D 471/08* (2006.01)

(52) U.S. Cl.
USPC .......................... 514/300; 546/113; 544/349

(58) Field of Classification Search
None
See application file for complete search history.

(56) References Cited

U.S. PATENT DOCUMENTS

| | | | |
|---|---|---|---|
| 4,922,901 | A | 5/1990 | Brooks et al. |
| 5,187,166 | A | 2/1993 | Kikuchi et al. |
| 5,583,140 | A | 12/1996 | Bencherif et al. |
| 5,585,388 | A | 12/1996 | Cosford et al. |
| 5,597,919 | A | 1/1997 | Dull et al. |
| 5,604,231 | A | 2/1997 | Smith et al. |
| 5,616,716 | A | 4/1997 | Dull et al. |
| 5,663,356 | A | 9/1997 | Ruecroft et al. |
| 5,672,601 | A | 9/1997 | Cignarella |
| 5,852,041 | A | 12/1998 | Cosford et al. |
| 5,853,696 | A | 12/1998 | Elmalech et al. |
| 5,952,339 | A | 9/1999 | Bencherif et al. |
| 5,969,144 | A | 10/1999 | London et al. |
| 6,310,043 | B1 | 10/2001 | Bundle et al. |
| 6,437,138 | B1 | 8/2002 | Lin et al. |
| 7,098,331 | B2 | 8/2006 | Schmidtt et al. |
| 2001/0056084 | A1 | 12/2001 | Allgeier et al. |
| 2003/0092700 | A1 | 5/2003 | Czollner et al. |
| 2007/0225492 | A1* | 9/2007 | Pinna et al. ................. 540/347 |

FOREIGN PATENT DOCUMENTS

| | | |
|---|---|---|
| EP | 0297858 | 1/1989 |
| GB | 2295387 | 5/1996 |
| WO | WO96/40682 | 12/1986 |
| WO | WO94/08992 | 4/1994 |
| WO | WO96/31475 | 10/1996 |
| WO | WO96/40682 | 12/1996 |
| WO | WO97/46554 | 12/1997 |
| WO | WO98/25619 | 6/1998 |
| WO | WO99/21834 | 5/1999 |
| WO | WO00/75110 | 12/2000 |
| WO | WO01/19817 | 3/2001 |
| WO | WO01/32264 | 5/2001 |
| WO | WO02/12245 | 2/2002 |
| WO | WO03/008559 | 1/2003 |
| WO | WO2004/078752 | 9/2004 |
| WO | WO2005/108402 | 11/2005 |
| WO | WO-2008/112473 | 9/2008 |
| WO | WO-2008/112734 | 9/2008 |
| WO | WO-2009/111550 | 9/2009 |

OTHER PUBLICATIONS

Loriga et al., "3-{2-[Bis-(4-fluorophenyl)methoxy]ethyl}-6-substituted-3,6-diazabicyclo[3.1.1]heptanes as novel potent dopamine uptake inhibitors," Bioorganic & Medicinal Chemistry 15 (2007), pp. 3748-3755.

Loriga et al., "Synthesis of 3,6-diazabicyclo[3.1.1]heptanes as novel ligands for the opioid receptors," Bioorganic & Medicinal Chemistry 14 (2006), pp. 676-691.

Arneric, et al., Neuronal nicotinic receptors: A perspective on two decades of drug discovery research, Biochemical Pharmacology, 74: 1092-1101 (2007).

Arneric, S., et al., "Cholinergic channel modulators as a novel therapeutic strategy for Alzheimer's disease," Exp. Opin. Invest. Drugs, 5(1): 79-100 (1996).

Arneric, S., et al., "Preclinical Pharmacology of ABT-418: A Prototypical Cholinergic Channel Activator for the Potential Treatment of Alzheimer's Disease," CNS Drug Rev., 1(1): 1-26 (1995).

Bannon, A. W., et al., "Broad-Spectrum, Non-Opioid Analgesic Activity by Selective Modulation of Neuronal Nicotinic Acetylcholine Receptors," Science, 279: 77-80 (1998).

Bencherif M. and R.J. Lukas, "Differential Regulation of Nicotinic Acetylcholine Receptor Expression by Human TE671/RD Cells Following Second Messenger Modulation and Sodium Butyrate Treatments," Mol Cell Neurosci., 2(1): 52-65 (1991).

(Continued)

Primary Examiner — Emily Bernhardt
(74) Attorney, Agent, or Firm — Womble Carlyle Sandridge & Rice, LLP; Amy H. Fix

(57) ABSTRACT

The present invention relates to compounds that bind to and modulate the activity of neuronal nicotinic acetylcholine receptors, to processes for preparing these compounds, to pharmaceutical compositions containing these compounds, and to methods of using these compounds for treating a wide variety of conditions and disorders, including those associated with dysfunction of the central nervous system (CNS).

6 Claims, 6 Drawing Sheets

(56) References Cited

OTHER PUBLICATIONS

Bencherif, M., and J. D. Schmitt, "Targeting Neuronal Nicotinic Receptors: a Path to New Therapies," Current Drug Targets, 1(4): 349-357 (2002).

Bencherif, M., and R.J. Lukas, "Ligand Binding and Functional Characterization of Muscarinic Acetylcholine Receptors on the TE671/RD Human Cell Line," J. Pharmacol. Exp. Ther., 257(3): 946-953 (1991).

Boess et al., "The Novel α7 Nicotinic Acetycholine Receptor Agonist N-[(3R)-1-Azabicyclo[2.2.2]oct-3-yl]-7-[2-(methoxy)phenyl]-1-benzofuran-2-carboxamide Improves Working and Recognition Memory in Rodents," The Journal of Pharmacology and Experimental Therapeutics, vol. 321, No. 2, 2007.

Bordia et al., "Continuous And Intermittent Nicotine Treatment Reduces L-3,4-Dihydroxyphenylalanine (L-Dopa)-Induced Dyskinesias in A Rat Model Of Parkinson's Disease," *J Pharmacol Exp Ther* 327: 239-47 (2008)).

Breining et al., "Neuronal Nicotinic Acetylcholine Receptor Modulators: Recent Advances and Therapeutic Potential," Annual Reports in Medicinal Chemistry, vol. 40, 2005.

Brioni, J.D., et al., "The Pharmacology of (−)-Nicotine and Novel Cholinergic Channel Modulators," *Adv. Pharmacol.*, 37: 153-214 (1997).

Brotchie et al., "Levodopa-Induced Dyskinesia in Parkinson's Disease," *J Neural Transm*, 112: 359-91 (2005).

Carta et al., "Serotonin-Dopamine Interaction In The Induction And Maintenance Of L-Dopa-Induced Dyskinesias," *Prog Brain Res*, 172: 465-78 (2008).

Cenci et al., "Post-Versus Presynaptic Plasticity in L-Dopa-Induced Dyskinesia,". *J Neurochem*, 99: 381-392 (2006).

Cenci et al., Animal models of neurological deficits: how relevant is the rat? *Nat Rev Neurosci* 3:574-579 (2002).

Cenci et al., L-DOPA-induced dyskinesia in the rat is associated with striatal overexpression of prodynorphin- and glutamic acid decarboxylase mRNA; *Eur J Neurosci* 10:2694-2706 (1998).

Cheng, Yung-Chi, and W.H. Prusoff, "Relationship Between the Inhibition Constant ($K_I$) and the Concentration of Inhibitor which Causes 50 Per Cent inhibition ($I_{50}$) of an Enzymatic Reaction," *Biochem. Pharmacol.*, 22(23): 3099-3108 (1973).

Chiari, A., et al., "Sex Differences in Cholinergic Analgesia I: A Supplemental Nicotinic Mechanism in Normal Females," *Anesthesiology*, 91(5): 1447-1454 (1999).

Coe et al., "3,5-Bicyclic Aryl Piperidines: A Novel Class of α4β2 Neuronal Nicotinic Receptor Partial Agonists for Smoking Cessation," Bioorganic & Medicinal Chemistry Letters 15 (2005), pp. 4889-4897.

Cox, H. et al., "The Selective Kappa-Opioid Receptor Agonist U50,488 Reduces L-Dopa-Induced Dyskinesias But Worsens Parkinsonism In MPTP-Treated Primates," *Exp Neurol*, (2007).

Damaj et al., "Enantioselective Effects of Hydroxy Metabolites of Bupropion on Behavior and on Function of Monoamine Transporters and Nicotinic Receptors," Molecular Pharmacology, vol. 66, No. 3, pp. 675-682, 2004.

Damaj, M.I., et al., "Analgesic Activity of Metanicotine, A Selective Nicotinic Agonist," *Society for Neuroscience*, 23: 669 ABSTRACT 266.9 (1997).

Damaj, M.I., et al., "Antinociceptive and Pharmacological Effects of Metanicotine, a Selective Nicotinic Agonist," *J. Pharmacol. Exp. Ther.*, 291(1): 390-398 (1999).

Dani et al., "Potential Applications of Nicotinic Ligands in the Laboratory and Clinic," Bioorganic & Medicinal Chemistry Letters 14, pp. 1837-1839, 2004.

Dani, J.A. & Bertrand, D., "Nicotinic Acetylcholine Receptors And Nicotinic Cholinergic Mechanisms Of The Central Nervous System," *Annu Rev Pharmacol Toxicol*, 47: 699-729 (2007).

Davies, A.R.L., et al., "Characterisation of the binding of [$^3$H]methyllycaconitine: a new radioligand for labeling α7-type neuronal nicotinic acetylcholine receptors," *Neuropharmacol.*, 38: 679-690 (1999).

Decina, P., et al., "Cigarette Smoking and Neuroleptic-Induced Parkinsonism," *Biol. Psychiatry*, 28(6): 502-508 (1990).

Decker et al., "Nicotinic Acetylcholine Receptor Agonists: A Potential New Class of Analgesics," Current Topics in Medicinal Chemistry, vol. 4, pp. 369-384, 2004.

Dekundy et al., "Modulation Of L-Dopa-Induced Abnormal Involuntary Movements By Clinically Tested Compounds: Further Validation Of The Rat Dyskinesia Model," *Behav Brain Res*, 179: 76-89 (2007).

Dwoskin et al., "Recent Developments in Neuronal Nicotinic Acetycholine Receptor Antagonists," Expert Opinion on Therapeutic Patents, pp. 1561-1581, 2000.

Dwoskin et al., A Novel Mechanism of Action and Potential Use for Lobeline as a Treatment for Lobeline as a Treatment for Psychostimulant Abuse, Biochemical Pharmacology 63, pp. 89-98, 2002.

Exley et al., "Presynaptic Nicotinic Receptors: A Dynamic And Diverse Cholinergic Filter Of Striatal Dopamine Neurotransmission," *Br J Pharmacol*, 153 Suppl 1: S283-97 (2008).

Fabbrini et al., "Levodopa-Induced Dyskinesias," *Mov Disord* (2007).

Fox et al., "Translation Of Nondopaminergic Treatments For Levodopa-Induced Dyskinesia From MPTP-Lesioned Nonhuman Primates To Phase IIA Clinical Studies: Keys To Success And Roads To Failure," *Mov Disord*, 21, 1578-94 (2006).

Gibson, S. et al., "Principal Components Describing Biological Activities and Molecular Diversity of Heterocyclic Aromatic Ring Fragments," *J. Med. Chem.*, 39: 4065-4072 (1996).

Gotti, C. et al., "Heterogeneity And Complexity Of Native Brain Nicotinic Receptors," *Biochem Pharmacol*, 74: 1102-11 (2007)

Grady, S.R. et al., "The Subtypes Of Nicotinic Acetylcholine Receptors On Dopaminergic Terminals Of Mouse Striatum," *Biochem Pharmacol*, 74: 1235-46 (2007).

Graham et al., "Human Brain Nicotinic Receptors, their Distribution and Participation in Neuropsychiatric Disorders," Current Drug Targets-CNS & Neurological Disorders, pp. 287-297, 2002.

Green et al., *Protecting Groups in Organic Synthesis*, $3^{rd}$ Edition, John Wiley & Sons (1999).

Greene et al., "Protective Groups in Organic Synthesis," Protective Groups In Organic Synthesis, 3rd ed.; John Wiley & Sons: New York, 1991.

Guigoni, C. et al., "Involvement of Sensorimotor, Limbic, and Associative Basal Ganglia Domains In L-3,4-Dihydroxyphenylalanine-Induced Dyskinesia," J Neurosci, 25: 2102-7 (2005).

Guigoni, C. et al., "Pathogenesis Of Levodopa-Induced Dyskinesia: Focus On D1 And D3 Dopamine Receptors," Parkinsonism Relat Disord, 11 Suppl 1: S25-9 (2005).

Hajos et al., "The Selective α7 Nicotinic Acetylcholine Receptor Agonist PNU-282987 [N-[(3R)-1-Azabicyclo[2.2.2]Oct-3-Yl]-4-Chlorobenzamide Hydrochloride] Enhances Gabaergic Synaptic Activity in Brain Slices and Restores Auditory Gating Deficits in Anesthetized Rats," The Journal of Pharmacology and Experimental Therapeutics, vol. 312, No. 3, 2005.

Hall, G.H. and D.M. Turner, "Effects of Nicotine on the Release of $^3$H-Noradrenaline from the Hypothalamus," *Biochemical Pharmacology*, 21: 1829-1838 (1972).

Hamon, M., "Neuropharmacology of anxiety: perspectives and prospects," *TiPS*, 15: 36-39 (1994).

Hansch, C., et al., "The Parabolic Dependence of Drug Action upon Lipophilic Characteras Revealed by a Study of Hypnotics," J. Med. Chem., 11(1): 1-11 (1967).

Harsing, Jr., L.G., et al., "Dopamine Efflux from Striatum After Chronic Nicotine: Evidence for Autoreceptor Desensitization," J. Neurochem., 59: 48-54 (1992).

Hery, F., et al., "Control of the Release of Newly Synthetized 3H-5-Hydroxytryptamine by Nicotinic and Muscarinic Receptors in Rat Hypothalamic Slices," Naunyn-Schmiedeberg's Arch. Pharmacol., 296: 91-97 (1977).

Hogg et al., "Nicotinic Acetylcholine Receptors as Drug Targets," Current Drug Targets-CNS & Neurological Disorders, pp. 123-130, 2004.

(56) References Cited

OTHER PUBLICATIONS

Holladay, M. W., et al., "Neuronal Nicotinic Acetylcholine Receptors as Targets for Drug Discovery," J. Med. Chem., 40(26): 4169-4194 (1997).
Hoyer, D. and H.W.G.M. Boddeke, "Partial agonists, full agonists, antagonists: dilemmas of definition," TiPS Reviews, 14: 270-275 (1993).
Hsu, A. et al., "Effect Of The D3 Dopamine Receptor Partial Agonist BP-897 [N-[4-(4-(2-Methoxyphenyl)Piperazinyl)Butyl]-2-Naphthamide] On L-3,4-Dihydroxyphenylalanine-Induced Dyskinesias And Parkinsonism In Squirrel Monkeys," J Pharmacol Exp Ther, 311: 770-7 (2004).
International Search Report (PCT/US2004/006530, dated Aug. 13, 2004).
Jain et al., "Modulators of Nicotinic Acetylcholine Receptors as Analgesics," Current Opinion in Investigational Drugs, vol. 5, pp. 76-81, 2004.
Jonnala et al., "Relationship Between the Increased Cell Surface α7 Nicotinic Receptor Expression and Neuroprotection Induced by Several Nicotinic Receptor Agonists," Journal of Neuroscience Research, vol. 66, pp. 565-572, 2001.
Lavand'homme, P., and J.C. Eisenach, "Sex Differences in Cholinergic Analgesia II: Differing Mechanisms in Two Models of Allodynia," Anesthesiology, 91(5): 1455-1461 (1999).
Levin, E.D., and A.H. Rezvani, "Nicotinic Treatment for Cognitive Dysfunction," Current Drug Targets: CNS and Neurological Disorders, 1(4): 423-431 (2002).
Linazasoro et al., "Pharmacological Treatment Of Parkinson's Disease: Life Beyond Dopamine D2/D3 Receptors?" J Neural Transm, 115: 431-41 (2008).
Linazasoro, G., "New Ideas On The Origin of L-Dopa-Induced Dyskinesias: Age, Genes and Neural Plasticity," Trends Pharmacol Sci, 26: 391-7 (2005).
Lippiello et al., The Binding of L-[$^3$H]Nicotine to a Single Class of High Affinity Sites in Rat Brain Membranes, The Journal of Pharmacology and Experimental Therapeutics, vol. 29, pp. 448-454, 1986.
Lippiello et al., "RJR-2403 A Nicotinic Agonist with CNS Selectivity II. In Vivo Characterization," The Journal of Pharmacology and Experimental Therapeutics, vol. 279, No. 3, pp. 1422-1429, 1996.
Lukas R.J., et al., "Characterization of Nicotinic Acetylcholine Receptors Expressed by Cells of the SH-SY5Y Human Neuroblastoma Clonal Line," Molec Cellular Neurosci., 4(1): 1-12 (1993).
Lukas, R.J., "Pharmacological Distinctions between Functional Nicotinic Acetylcholine Receptors on the PC12 Rat Pheochromocytoma and the TE671 Human Medulloblastoma," J. Pharmacol. Exp. Ther., 251(1): 175-182 (1989).
Lukas, R.J., and M.J. Cullen, "An Isotopic Rubidium Ion Efflux Assay for the Functional Characterization of Nicotinic Acetylcholine Receptors on Clonal Cell Lines," Anal. Biochem., 175(1): 212-218 (1988).
Luther, et al., "A Muscle Acetylcholine Receptor is Expressed in the Human Cerebellar Medulloblastoma Cell Line," J. Neurosci., 9(3): 1082-1096 (1989).
Marks, M.J., et al., "Nicotinic Binding Sites in Rat and Mouse Brain: Comparison of Acetylcholine, Nicotine, and α-Bungarotoxin," Mol. Pharmacol., 30(5): 427-436 (1986).
Marrero et al., "The Neuroprotective Effect of 2-(3-Pyridyl)-1-azabicylo[3.2.2]nonane (TC-1698), a Novel α7 Ligand, is Prevented through Angiotensin II Activation of a Tyrosine Phosphatase," The Journal of Pharmacology and Experimental Therapeutics, vol. 309, No. 1, pp. 16-27, 2003.
McEvoy et al., "The Importance of Nicotinic Acetylcholine Receptors in Schizophrenia, Bipolar Disorder and Tourette's Syndrome," Current Drug Targets-CNS & Neurological Disorders, pp. 433-442, 2002.
Mercuri, N.B. & Bernardi, G., "The 'Magic' Of L-Dopa: Why Is It The Gold Standard Parkinson's Disease Therapy?" Trends Pharmacol Sci, 26: 341-4 (2005).

Meredith et al., "Behavioral Models Of Parkinson's Disease In Rodents: A New Look At An Old Problem," Mov Disord, 21: 1595-606 (2006).
Miao et al., "Central Terminals of Nociceptors are Targets for Nicotine Suppression of Inflammation," Neuroscience, vol. 123, pp. 777-784, 2004.
Newhouse et al., "Effects of Nicotinic Stimulation on Cognitive Performance," Current Opinion in Pharmacology, vol. 4, pp. 36-46, 2004.
O'Neill, M.J., et al., "The Role of Neuronal Nicotinic Acetylcholine Receptors in Acute and Chronic Neurodegeneration," Current Drug Targets: CNS and Neurological Disorders, 1(4): 399-411 (2002).
Olanow et al., "Continuous Dopamine-Receptor Treatment of Parkinson's Disease: Scientific Rationale and Clinical Implications," Lancet Neurol, 5: 677-87 (2006).
Onaivi, E.S., et al., "Chronic Nicotine Reverses Age-Associated Increases in Tail-Flick Latency and Anxiety in Rats," Life Sciences, 54(3): 193-202 (1993).
Oswald, R.E., at al., "Characterization of nicotinic acetylcholine receptor channels of the TE671 human medulloblastoma clonal line," Neurosci. Lett., 96: 207-212 (1989).
Perez et al., "Long-Term Nicotine Treatment Differentially Regulates Striatal α6α4β2* and α6(Nonα4)β2* nAChR Expression and Function," Mol Pharmacol., Sep. 2008;74(3), pp. 844-853.
Perez et al., "Prominent role of α3/α6β2 * nAChRs In Regulating Evoked Dopamine Release In Primate Putamen: Effect Of Long-Term Nicotine Treatment," Mol Pharmacol., Apr. 2009;75(4); pp. 938-946.
Perez et al., "A6β2* And A4β2* Nicotinic Receptors Both Regulate Dopamine Signaling with Increased Nigrostriatal Damage: Relevance to Parkinson's Disease," Mol Pharmacol., Nov. 2010;78(5); pp. 971-980.
Pomerleau, O.F., et al., "The Effects of Cigarette Smoking on Pain and Anxiety," Addictive Behaviors, 9: 265-271 (1984).
Pullen, R.D., et al. "Transdermal Nicotine for Active Ulcerative Colitis," New England J. Med., 330(12): 811-815 (1994).
Quik et al., "Chronic Oral Nicotine Treatment Protects Against Striatal Degeneration in MPTP-Treated Treated Primates," J Neurochem, 98: 1866-75 (2006).
Quik et al., "Differential Nicotinic Receptor Expression In Monkey Basal Ganglia: Effects Of Nigrostriatal Damage," Neuroscience, 112: 619-30 (2002).
Quik et al., "Expression Of D(3) Receptor Messenger RNA And Binding Sites In Monkey Striatum And Substantia Nigra After Nigrostriatal Degeneration: Effect Of Levodopa Treatment," Neuroscience, 98: 263-73 (2000).
Quik et al., "Increases In Striatal Preproenkephalin Gene Expression Are Associated With Nigrostriatal Damage But Not L-Dopa-Induced Dyskinesias In The Squirrel Monkey," Neuroscience, 113: 213-20 (2002).
Quik et al., "L-Dopa Treatment Modulates Nicotinic Receptors In Monkey Striatum," Mol Pharmacol, 64: 619-28 (2003).
Quik et al., "Multiple Roles for Nicotine in Parkinson's Disease," Biochemical Pharmacology 78 (2009); pp. 677-685.
Quik et al., "nAChR Agonists reduce L-dopa-induced Dyskinesias in Parkinsonisan Rats," Biochemical Pharmacology 78 (2009), pp. 899-925.
Quik et al., "Nicotine and Parkinson's Disease: Implications For Therapy," Mov Disord, 23: 1641-52 (2008).
Quik et al., "Nicotine Neuroprotection Against Nigrostriatal Damage: Importance of the Animal Model," vol. 28, Issue 5, May 2007, pp. 229-235.
Quik et al., "Nicotine Reduces Levodopa-Incuded Dyskinesias in Lesioned Monkeys," Ann. Neurol. 2007; 62, pp. 588-596.
Quik et al., "Nicotine Reduces Levodopa-Induced Dyskinesias In Lesioned Monkeys," Annals of Neurology,62: 588-96 (2007).
Quik et al., "Nicotinic Receptors As CNS Targets for Parkinson's Disease,". Biochem Pharmacol, 74: 1224-1234 (2007).
Quik et al., "Striatal α6* Nicotinic Acetylcholine Receptors: Potential Targets for Parkinson's Disease Therapy," The Journal of Pharmacology and Experimental Therapeutics, vol. 316, No. 2, 2006, pp. 481-489.

(56) References Cited

OTHER PUBLICATIONS

Quik, Smoking, Nicotine and Parkinson's Disease, Trends in Neuroscience, vol. 27, No. 9, Sep. 2004, pp. 561-568.
Rapier, C., et al., "Stereoselective Nicotine-Induced Release of Dopamine from Striatal Synaptosomes: Concentration Dependence and Repetitive Stimulation," J. Neurochem., 50(4): 1123-1130 (1988).
Ripoll et al., Nicotinic Receptors and Schizophrenia, Current Medical Research and Opinions, vol. 20, No. 7, pp. 1057-1074, 2004.
Robinson, Medical Therapy of Inflammatory Bowel Disease for the 21st Century, Eur. J. Surg.; Suppl. 582: 90-98 (1998).
Romano, C., and A. Goldstein, "Stereospecific Nicotine Receptors on Rat Brain Membranes," Science, 210: 647-650 (1980).
Rowell, P.P. and D.L. Winkler, "Nicotinic Stimulation of [$^3$H] Acetylcholine Release from Mouse Cerebral Cortical Synaptosomes," J. Neurochem., 43(6): 1593-1598 (1984).
Sacco et al., "Nicotinic Receptor Mechanisms and Cognition in Normal States and Neuropsychiatric Disorders," Journal of Psychopharmacology, vol. 18, pp. 457-474, 2004.
Samadi, P., Bedard, P.J. & Rouillard, C., "Opioids And Motor Complications In Parkinson's Disease," Trends Pharmacol Sci, 27: 512-7 (2006).
Sanberg, P.R., et al., "Nicotine Potentiation of Haloperidol-Induced Catalepsy: Striatal Mechanisms," Pharmacol. Biochem. & Behavior, 46: 303-307 (1993).
Sandor, N.T., et al. "Effect of nicotine on dopaminergic-cholinergic interaction in the striatum," Brain Res., 567: 313-316 (1991).
Schmitt, J.D., and M. Bencherif, "Chapter 5. Targeting Nicotinic Acetylcholine Receptors: Advances in Molecular Design and Therapies," Ann. Rep. Med. Chem., 35: 41-51 (2000).
Schneider et al., "Effects of SIB-1508Y, a Novel Neuronal Nicotinic Acetycholine Receptor Agonist, on Motor Behavior in Parkinsonisan Monkeys," Movement Disorders, vol. 13, No. 4, 1998, pp. 637-642.
Shytle et al., Neuronal Nicotinic Receptor Inhibition for Treating Mood Disorders: Preliminary Controlled Evidence with Mecamylamine, Depression and Anxiety, vol. 16, pp. 89-92, 2002.
Shytle et al., "Nicotinic Acetylcholine Receptors as Targets for Antidepressants," Moelcular Psychiatry, vol. 7, pp. 525-535, 2002.
Silva, N.M., et al., "New isoxazole derivatives designed as nicotinic acetylcholine receptor ligand candidates," Eur. J. Med. Chem., 37: 163-170 (2002).
Sjak-Shie, N.N. and E.M. Meyer, "Effects of chronic nicotine and pilocarpine administration on neocortocal neuronal density and [3H]GABA uptake in nucleus basalis lesioned rats," Brain Res., 624: 295-298 (1993).
Stacy et al., "Optimizing Long-Term Therapy For Parkinson Disease: Options For Treatment-Associated Dyskinesia,". Clin Neuropharmacol, 31: 120-5 (2008).
Stacy et al., "Optimizing Long-Term Therapy For Parkinson Disease: Levodopa, Dopamine Agonists, And Treatment-Associated Dyskinesia," Clin Neuropharmacol, 31: 51-6 (2008).
Stratton, M.R., et al., "Characterization of the human cell line TE671," Carcinogenesis, 10(5): 899-905 (1989).
Suto et al., "Neuronal Nicotinic Acetylcholine Receptors as Drug Targets," Expert Opinion on Therapeutic Targets, vol. 8, pp. 61-64, 2004.
Thanvi et al., "Levodopa-Induced Dyskinesia In Parkinson's Disease: Clinical Features, Pathogenesis, Prevention And Treatment," Postgrad Med J, 83: 384-8 (2007).
Tillerson et al., "Forced Limb-Use Effects On The Behavioral And Neurochemical Effects Of 6-Hydroxydopamine," J Neurosci 21, 4427-35 (2001).
Toth, E., et al., "Effect of Nicotine of Extracellular Levels of Neurotransmitters Assessed by Microdialysis in Various Brain Regions: Role of Glutamic Acid," Neurochem. Res., 17(3): 265-270 (1992).
Tracey et al., "The Inflammatory Reflex," Nature, vol. 420, 2002, pp. 853-859.
Tripathi, H.L., et al., "Nicotine-Induced Antinociception of Rats and Mice: Correlation with Nicotine Brain Levels," J. Pharmacol. Exp. Ther., 221(1): 91-96 (1982).
Vincler, "Neuronal Nicotinic Receptors as Targets for Novel Analgesics," Expert Opin. Investig. Drugs, vol. 14, pp. 1191-1196, 2005.
Vizi, E.S., "Acetylcholine release from guinea-pig ileum by parasympathetic ganglion stimulants and gastrin-like polypeptides," Br. J. Pharmac., 47: 765-777 (1973).
Wagner, B., et al., "Does Smoking Reduce the Risk of Neuroleptic Parkinsonoids?," Pharmacopsychiat., 21: 302-303 (1988).
Whiting, P.J., et al., "Expression of nicotinic acetylcholine receptor subtypes in brain and retina," Brain Res Mol Brain Res., 10(1): 61-70 (1991).
Whiting, P.J., et al., "Functional acetylcholine receptor in PC12 cells reacts with a monoclonal antibody to brain nicotinic receptors," Nature, 327(6122): 515-518(1987).
Williams, M., et al., "Neuronal Nicotinic Acetylcholine Receptors," DN&P, 7(4): 205-223 (1994).
Yang et al., "Associated Alterations of Striatal Dopamine D2/D3 Receptor and Transporter Binding in Drug-Naive Patients With Schizophrenia: A Dual-Isotope SPECT Study," Am J Psychiatry vol. 161:8, pp. 1496-1498, Aug. 2004.
Young et al., "Mecamylamine: New Therapeutic Uses and Toxicity/ Risk Profile," Clinical Therapeutics, Bol 23, No. 4, 2001, pp. 532-565.

\* cited by examiner

3,6-DIAZABICYCLO[3.1.1]HEPTANES AS NEURONAL NICOTINIC ACETYCHOLINE RECEPTOR LIGANDS

CROSS REFERENCE TO RELATED APPLICATION

This application claims priority to PCT Application Number PCT/US2010/058836, with an International Filing Date of Dec. 3, 2010; which claims priority to U.S. Provisional Patent Application Ser. No. 61/267,218, filed Dec. 7, 2009, each of which is herein incorporated by reference in its entirety.

FIELD OF THE INVENTION

The present invention relates to compounds that bind to and modulate the activity of neuronal nicotinic acetylcholine receptors, to processes for preparing these compounds, to pharmaceutical compositions containing these compounds, and to methods of using these compounds for treating a wide variety of conditions and disorders, including those associated with dysfunction of the central nervous system (CNS).

BACKGROUND OF THE INVENTION

The therapeutic potential of compounds that target neuronal nicotinic receptors (NNRs), also known as nicotinic acetylcholine receptors (nAChRs), has been the subject of several reviews. See, for example, Arneric et al., *Biochem. Pharmacol.* 74: 1092 (2007), Breining et al., *Ann. Rep. Med. Chem.* 40: 3 (2005), Hogg and Bertrand, *Curr. Drug Targets: CNS Neurol. Disord.* 3: 123 (2004), Suto and Zacharias, *Expert Opin. Ther. Targets* 8: 61 (2004), Dani et al., *Bioorg. Med. Chem. Lett.* 14: 1837 (2004), Bencherif and Schmitt, *Curr. Drug Targets: CNS Neurol. Disord.* 1: 349 (2002), Yang et al., *Acta Pharmacol. Sin.* 30(6): 740-751 (2009). Among the kinds of indications for which NNR ligands have been proposed as therapies are cognitive disorders, including Alzheimer's disease, attention deficit disorder, and schizophrenia (Biton et al., *Neuropsychopharm.* 32: 1 (2007), Boess et al., *J. Pharmacol. Exp. Ther.* 321: 716 (2007), Hajos et al., *J. Pharmacol. Exp. Ther.* 312: 1213 (2005), Newhouse et al., *Curr. Opin. Pharmacol.* 4: 36 (2004), Levin and Rezvani, *Curr. Drug Targets: CNS Neurol. Disord.* 1: 423 (2002), Graham et al., *Curr. Drug Targets: CNS Neurol. Disord.* 1: 387 (2002), Ripoll et al., *Curr. Med. Res. Opin.* 20(7): 1057 (2004), and McEvoy and Allen, *Curr. Drug Targets: CNS Neurol. Disord.* 1: 433 (2002)); pain and inflammation (Decker et al., *Curr. Top. Med. Chem.* 4(3): 369 (2004), Vincler, *Expert Opin. Invest. Drugs* 14(10): 1191 (2005), Jain, *Curr. Opin. Inv. Drugs* 5: 76 (2004), Miao et al., *Neuroscience* 123: 777 (2004)); depression and anxiety (Shytle et al., *Mol. Psychiatry* 7: 525 (2002), Damaj et al., *Mol. Pharmacol.* 66: 675 (2004), Shytle et al., *Depress. Anxiety* 16: 89 (2002)); neurodegeneration (O'Neill et al., *Curr. Drug Targets: CNS Neurol. Disord.* 1: 399 (2002), Takata et al., *J. Pharmacol. Exp. Ther.* 306: 772 (2003), Marrero et al., *J. Pharmacol. Exp. Ther.* 309: 16 (2004)); Parkinson's disease (Bordia et al., *J. Pharmacol. Exp. Ther.* 327: 239 (2008), Jonnala and Buccafusco, *J. Neurosci. Res.* 66: 565 (2001)); addiction (Dwoskin and Crooks, *Biochem. Pharmacol.* 63: 89 (2002), Coe et al., *Bioorg. Med. Chem. Lett.* 15(22): 4889 (2005)); obesity (Li et al., *Curr. Top. Med. Chem.* 3: 899 (2003)); and Tourette's syndrome (Sacco et al., *J. Psychopharmacol.* 18(4): 457 (2004), Young et al., *Clin. Ther.* 23(4): 532 (2001)).

There exists a heterogeneous distribution of nAChR subtypes in both the central and peripheral nervous systems. For instance, the α4β2, α6 containing, α7, and α3β2 subtypes are predominant in vertebrate brain, whereas the α3β4 subtype is predominate at the autonomic ganglia, and the α1β1δγ and α1β1δε subtypes are predominant at the neuromuscular junction (see Dwoskin et al., *Exp. Opin. Ther. Patents* 10: 1561 (2000) and Holliday et al. *J. Med. Chem.* 40(26), 4169 (1997)). Compounds which selectively target the CNS predominant subtypes have potential utility in treating various CNS disorders. However, a limitation of some nicotinic compounds is that they lack the selectivity required to preferentially target CNS receptors over receptor located in the muscle and ganglion. Such drugs are often associated with various undesirable side effects. Therefore, there is a need to have compounds, compositions, and methods for preventing or treating various conditions or disorders where the compounds exhibit a high enough degree of nAChR subtype specificity to elicit a beneficial effect, without significantly affecting those receptor subtypes which have the potential to induce undesirable side effects, including, for example, appreciable activity at cardiovascular and skeletal muscle sites.

SUMMARY OF THE INVENTION

The present invention includes compounds which bind with high affinity to NNRs of either the α4β2 subtype, or the α6-containing subtype, or both NNR subtypes. The present invention also relates to pharmaceutically acceptable salts prepared from these compounds.

The present invention includes pharmaceutical compositions comprising a compound of the present invention or a pharmaceutically acceptable salt thereof. The pharmaceutical compositions of the present invention can be used for treating or preventing a wide variety of conditions or disorders, particularly those disorders mediated by nicotinic acetylcholine receptors.

The present invention includes a method for treating, preventing, delaying the onset of, or slowing the progression of disorders mediated by nicotinic acetylcholine receptors, in mammals in need of such treatment. The methods involve administering to a subject a therapeutically effective amount of a compound of the present invention, including a salt thereof, or a pharmaceutical composition that includes such compounds.

DETAILED DESCRIPTION OF THE INVENTION

I. Compounds

Figure 1:
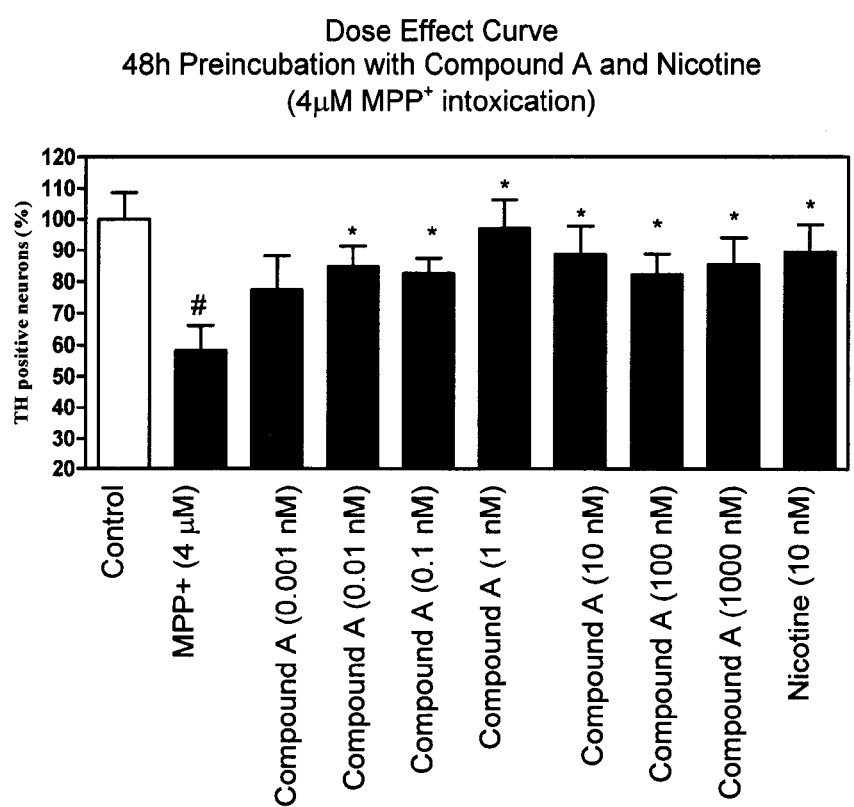
FIG. 1 illustrates a dose effect curve of Compound A (3-cyclopropylcarbonyl-3,6-diazabicyclo[3.1.1], as the heptane dip-toluoyl-D-tartrate salt) and nicotine on TH positive neurons after 48 h pretreatment, followed by MPP$^+$ injury (4 μM, 48 h).

The present invention includes compounds of Formula I:

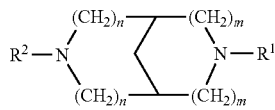

Formula I wherein:
each m is identical and is 0 or 1;
each n is identical and is 0 or 1;
when each m is 0, then each n is 1;
when each m is 1, then each n is 0;
$R^1$ is
—C(O)—$R^3$,
—C(O)O—$R^3$,
—C(O)NH—$R^3$,
—C(O)—$(CH_2)_q$—X—$R^3$,
—C(O)O—$(CH_2)_q$—X—$R^3$, or
—C(O)NH—$(CH_2)_q$—X—$R^3$;
q is 1, 2, 3, 4, 5, or 6;
X is —O—, —S—, —NH—, or —NHC(O)—;
$R^2$ is H or alkyl;
$R^3$ is alkyl, alkenyl, alkynyl, cycloalkyl, cycloalkenyl, cycloalkynyl, aryl, heteroaryl, or heterocyclic;
each $R^3$ individually may be optionally substituted with one or more alkyl, alkenyl, alkynyl, aryl, aryloxy, amino, amido, heteroaryl, halogen, hydroxyl, alkoxy, cycloalkyl, cycloalkenyl, cycloalkynyl, heterocyclic, or alkylamido substituents;
with the proviso that Formula I does not include the following compounds:
3-ethylcarbonyl-3,6-diazabicyclo[3.1.1]heptane,
6-ethylcarbonyl-3,6-diazabicyclo[3.1.1]heptane,
6-tert-butoxycarbonyl-3,6-diazabicyclo[3.1.1]heptane;
or a pharmaceutically acceptable salt thereof.
The present invention includes compounds of Formula I:

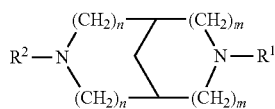

Formula I wherein:
each m is identical and is 0 or 1;
each n is identical and is 0 or 1;
when each m is 0, then each n is 1;
when each m is 1, then each n is 0;

$R^1$ is
—C(O)—$R^{3A}$,
—C(O)O—$R^{3B}$,
—C(O)NH—$R^{3C}$,
—C(O)—$(CH_2)_q$—X—$R^{3C}$,
—C(O)O—$(CH_2)_q$—X—$R^{3C}$, or
—C(O)NH—$(CH_2)_q$—X—$R^{3C}$;
q is 1, 2, 3, 4, 5, or 6;
X is —O—, —S—, —NH—, or —NHC(O)—;
$R^2$ is H or alkyl;
when $R^2$ is H, then $R^{3A}$ is methyl, propyl, butyl, pentyl, hexyl, alkenyl, alkynyl, cycloalkyl, cycloalkenyl, cycloalkynyl, aryl, heteroaryl, or heterocyclic;
when $R^2$ is alkyl, then $R^{3A}$ is methyl, ethyl, propyl, butyl, pentyl, hexyl, alkenyl, alkynyl, cycloalkyl, cycloalkenyl, cycloalkynyl, aryl, heteroaryl, or heterocyclic;
when $R^2$ is H and each m is 0 and each n is 1, then $R^{3B}$ is methyl, ethyl, propyl, n-butyl, isobutyl, sec-butyl, pentyl, hexyl, alkenyl, alkynyl, cycloalkyl, cycloalkenyl, cycloalkynyl, aryl, heteroaryl, or heterocyclic;
when $R^2$ is H and each m is 1 and each n is 0, or when $R^2$ is alkyl, then $R^{3B}$ is methyl, ethyl, propyl, butyl, pentyl, hexyl, alkenyl, alkynyl, cycloalkyl, cycloalkenyl, cycloalkynyl, aryl, heteroaryl, or heterocyclic;
each $R^{3C}$ individually is alkyl, alkenyl, alkynyl, cycloalkyl, cycloalkenyl, cycloalkynyl, aryl, heteroaryl, or heterocyclic;
each $R^3$ individually may be optionally substituted with one or more alkyl, alkenyl, alkynyl, aryl, aryloxy, amino, amido, heteroaryl, halogen, hydroxyl, alkoxy, cycloalkyl, cycloalkenyl, cycloalkynyl, heterocyclic, or alkylamido substituents;
or a pharmaceutically acceptable salt thereof.

In one embodiment, a compound is selected from the group consisting of:
3-methylcarbonyl-3,6-diazabicyclo[3.1.1]heptane;
3-isopropylcarbonyl-3,6-diazabicyclo[3.1.1]heptane;
3-cyclopropylcarbonyl-3,6-diazabicyclo[3.1.1]heptane;
3-propoxycarbonyl-3,6-diazabicyclo[3.1.1]heptane;
3-isopropoxycarbonyl-3,6-diazabicyclo[3.1.1]heptane:
3-methoxyethoxycarbonyl-3,6-diazabicyclo[3.1.1]heptane;
3-(2-fluoroethoxy)carbonyl-3,6-diazabicyclo[3.1.1]heptane;
3-(2-bromofuran-5-yl)carbonyl-3,6-diazabicyclo[3.1.1]heptane;
3-(3-bromofuran-5-yl)carbonyl-3,6-diazabicyclo[3.1.1]heptane;
3-(3-chlorofuran-2-yl)carbonyl-3,6-diazabicyclo[3.1.1]heptane;
3-(isoxazol-5-yl)carbonyl-3,6-diazabicyclo[3.1.1]heptane;
3-(2-methoxyethyl)carbonyl-3,6-diazabicyclo[3.1.1]heptane;
3-(2,2,2-trifluoroethyl)carbonyl-3,6-diazabicyclo[3.1.1]heptane;
3-(tetrahydrofuran-3-yl)carbonyl-3,6-diazabicyclo[3.1.1]heptane;
6-(2-chlorofuran-5-yl)carbonyl-3,6-diazabicyclo[3.1.1]heptane;
6-(2-bromorofuran-5-yl)carbonyl-3,6-diazabicyclo[3.1.1]heptane;
6-cyclobutylcarbonyl-3,6-diazabicyclo[3.1.1]heptane;
6-(2-methoxyethyl)carbonyl-3,6-diazabicyclo[3.1.1]heptane;
cis-3-(2-fluorocycloprop-1-yl)carbonyl-3,6-diazabicyclo[3.1.1]heptane;
trans-3-(2-fluorocycloprop-1-yl)carbonyl-3,6-diazabicyclo[3.1.1]heptane;
cis-6-(2-fluorocycloprop-1-yl)carbonyl-3,6-diazabicyclo[3.1.1]heptane; and trans-6-(2-fluorocycloprop-1-yl)carbonyl-3,6-diazabicyclo [3.1.1]heptane;

or a pharmaceutically acceptable salt thereof.

In one embodiment, the present invention is compound, 3-cyclopropylcarbonyl-3,6-diazabicyclo[3.1.1]heptane, Compound A, or a pharmaceutically acceptable salt thereof.

One aspect of the present invention includes a pharmaceutical composition comprising a compound of the present invention and a pharmaceutically acceptable carrier.

One aspect of the present invention includes a method for the treatment or prevention of a disease or condition mediated by neuronal nicotinic receptors comprising the administration of a compound of the present invention. In one embodiment, the neuronal nicotinic receptors are of the α4β2 subtype. In one embodiment, the neuronal nicotinic receptors are of the α6-containing subtype. In one embodiment, the neuronal nicotinic receptors are a combination of the α4β2 and α6-containing subtypes.

One aspect of the present invention includes use of a compound of the present invention for the preparation of a medicament for the treatment or prevention of a disease or condition mediated by neuronal nicotinic receptors comprising the administration of a compound of the present invention. In one embodiment, the neuronal nicotinic receptors are of the α4β2 subtype. In one embodiment, the neuronal nicotinic receptors are of the α6-containing subtype. In one embodiment, the neuronal nicotinic receptors are a combination of the α4β2 and α6-containing subtypes.

One aspect of the present invention includes a compound of the present invention for use as an active therapeutic substance. One aspect, thus, includes a compound of the present invention for use in the treatment or prevention of a disease or condition mediated by neuronal nicotinic receptors comprising the administration of a compound of the present invention. In one embodiment, the neuronal nicotinic receptors are of the α4β2 subtype. In one embodiment, the neuronal nicotinic receptors are of the α6-containing subtype. In one embodiment, the neuronal nicotinic receptors are a combination of the α4β2 and α6-containing subtypes.

The scope of the present invention includes all combinations of aspects and embodiments.

The following definitions are meant to clarify, but not limit, the terms defined. If a particular term used herein is not specifically defined, such term should not be considered indefinite. Rather, terms are used within their accepted meanings.

As used throughout this specification, the preferred number of atoms, such as carbon atoms, will be represented by, for example, the phrase "$C_{x-y}$ alkyl," which refers to an alkyl group, as herein defined, containing the specified number of carbon atoms. Similar terminology will apply for other preferred terms and ranges as well. Thus, for example, $C_{1-6}$ alkyl represents a straight or branched chain hydrocarbon containing one to six carbon atoms.

As used herein the term "alkyl" refers to a straight or branched chain hydrocarbon, which may be optionally substituted, with multiple degrees of substitution being allowed. Examples of "alkyl" as used herein include, but are not limited to, methyl, ethyl, propyl, isopropyl, isobutyl, n-butyl, tert-butyl, isopentyl, and n-pentyl.

As used herein, the term "cycloalkyl" refers to a fully saturated optionally substituted monocyclic, bicyclic, or bridged hydrocarbon ring, with multiple degrees of substitution being allowed. Exemplary "cycloalkyl" groups as used herein include, but are not limited to, cyclopropyl, cyclobutyl, cyclopentyl, cyclohexyl, and cycloheptyl.

As used herein, the term "heterocycle" or "heterocyclyl" refers to an optionally substituted mono- or polycyclic ring system, optionally containing one or more degrees of unsaturation, and also containing one or more heteroatoms, which may be optionally substituted, with multiple degrees of substitution being allowed. Exemplary heteroatoms include nitrogen, oxygen, or sulfur atoms, including N-oxides, sulfur oxides, and dioxides. Preferably, the ring is three to twelve-membered, preferably three- to eight-membered and is either fully saturated or has one or more degrees of unsaturation. Such rings may be optionally fused to one or more of another heterocyclic ring(s) or cycloalkyl ring(s). Examples of "heterocyclic" groups as used herein include, but are not limited to, tetrahydrofuran, pyran, tetrahydropyran, 1,4-dioxane, 1,3-dioxane, piperidine, pyrrolidine, morpholine, tetrahydrothiopyran, and tetrahydrothiophene.

As used herein, the term "aryl" refers to a single benzene ring or fused benzene ring system which may be optionally substituted, with multiple degrees of substitution being allowed. Examples of "aryl" groups as used include, but are not limited to, phenyl, 2-naphthyl, 1-naphthyl, anthracene, and phenanthrene. Preferable aryl rings have five- to ten-members.

As used herein, a fused benzene ring system encompassed within the term "aryl" includes fused polycyclic hydrocarbons, namely where a cyclic hydrocarbon with less than maximum number of noncumulative double bonds, for example where a saturated hydrocarbon ring (cycloalkyl, such as a cyclopentyl ring) is fused with an aromatic ring (aryl, such as a benzene ring) to form, for example, groups such as indanyl and acenaphthalenyl, and also includes such groups as, for non-limiting examples, dihydronaphthalene and tetrahydronaphthalene.

As used herein, the term "heteroaryl" refers to a monocyclic five to seven membered aromatic ring, or to a fused bicyclic aromatic ring system comprising two of such aromatic rings, which may be optionally substituted, with multiple degrees of substitution being allowed. Preferably, such rings contain five- to ten-members. These heteroaryl rings contain one or more nitrogen, sulfur, and/or oxygen atoms, where N-oxides, sulfur oxides, and dioxides are permissible heteroatom substitutions. Examples of "heteroaryl" groups as used herein include, but are not limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinoxaline, benzofuran, benzoxazole, benzothiophene, indole, indazole, benzimidazole, imidazopyridine, pyrazolopyridine, and pyrazolopyrimidine.

As used herein, multiple degrees of substitution includes substitution with one or more alkyl, halo, haloalkyl, alkoxy, alkylthio, aryloxy, arylthio, —$NR^aR^b$, —$C(=O)NR^aR^b$, —$NR^aC(=O)R^b$, —$C(=O)R^a$, —$C(=O)OR^a$, —$OC(=O)R^a$, —$O(CR^aR^b)_{1-6}C(=O)R^a$, —$O(CR^aR^b)_dNR^bC(=O)R^a$, —$O(CR^aR^b)_{1-6}NR^bSO_2R^a$, —$OC(=O)NR^aR^b$, —$NR^aC(=O)OR^b$, —$SO_2R^a$, —$SO_2NR^aR^b$, or —$NR^2SO_2R^3$; where each $R^a$ and $R^b$ individually is hydrogen, alkyl, cycloalkyl, heterocyclyl, aryl, or arylalkyl, or $R^a$ and $R^b$ can combine with the atoms to which they are attached to form a 3- to 10-membered ring. Thus, as one example, Cy may be pyridinyl which may be substituted first by a halogen, such as F, and second by an alkoxy, such as —$OCH_3$.

As used herein the term "halogen" refers to fluorine, chlorine, bromine, or iodine.

As used herein the term "haloalkyl" refers to an alkyl group, as defined herein, which is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —$CF_3$.

As used herein the term "alkoxy" refers to a group —$OR^a$, where $R^a$ is alkyl as herein defined. Likewise, the term "alkylthio" refers to a group —$SR^a$, where $R^a$ is alkyl as herein defined.

As used herein the term "aryloxy" refers to a group —$OR^a$, where $R^a$ is aryl as herein defined. Likewise, the term "arylthio" refers to a group —$SR^a$, where $R^a$ is aryl as herein defined.

As used herein "amino" refers to a group —$NR^a R^b$, where each of $R^a$ and $R^b$ is hydrogen. Additionally, "substituted amino" refers to a group —$NR^a R^b$ wherein each of $R^a$ and $R^b$ individually is alkyl, alkenyl, alkynyl, cycloalkyl, aryl, heterocylcyl, or heteroaryl. As used herein, when either $R^a$ or $R^b$ is other than hydrogen, such a group may be referred to as a "substituted amino" or, for example if $R^a$ is H and $R^b$ is alkyl, as an "alkylamino."

As used herein, the term "pharmaceutically acceptable" refers to carrier(s), diluent(s), excipient(s) or salt forms of the compounds of the present invention that are compatible with the other ingredients of the formulation and not deleterious to the recipient of the pharmaceutical composition.

As used herein, the term "pharmaceutical composition" refers to a compound of the present invention optionally admixed with one or more pharmaceutically acceptable carriers, diluents, or excipients. Pharmaceutical compositions preferably exhibit a degree of stability to environmental conditions so as to make them suitable for manufacturing and commercialization purposes.

As used herein, the terms "effective amount", "therapeutic amount", and "effective dose" refer to an amount of the compound of the present invention sufficient to elicit the desired pharmacological or therapeutic effects, thus resulting in an effective treatment of a disorder. Treatment of a disorder may be manifested by delaying or preventing the onset or progression of the disorder, as well as the onset or progression of symptoms associated with the disorder. Treatment of a disorder may also be manifested by a decrease or elimination of symptoms, reversal of the progression of the disorder, as well as any other contribution to the well being of the patient.

The effective dose can vary, depending upon factors such as the condition of the patient, the severity of the symptoms of the disorder, and the manner in which the pharmaceutical composition is administered. Typically, to be administered in an effective dose, compounds may be administered in an amount of less than 5 mg/kg of patient weight. The compounds may be administered in an amount from less than about 1 mg/kg patient weight to less than about 100 μg/kg of patient weight, and further between about 1 μg/kg to less than 100 μg/kg of patient weight. The foregoing effective doses typically represent that amount that may be administered as a single dose, or as one or more doses that may be administered over a 24 hours period.

The compounds of this invention may be made by a variety of methods, including well-established synthetic methods. Illustrative general synthetic methods are set out below and then specific compounds of the invention are prepared in the working Examples.

In the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1999) *Protecting Groups in Organic Synthesis*, $3^{rd}$ Edition, John Wiley & Sons, herein incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention.

The present invention also provides a method for the synthesis of compounds useful as intermediates in the preparation of compounds of the present invention along with methods for their preparation.

The compounds can be prepared according to the methods described below using readily available starting materials and reagents. In these reactions, variants may be employed which are themselves known to those of ordinary skill in this art but are not described in detail here.

Unless otherwise stated, structures depicted herein are also meant to include compounds which differ only in the presence of one or more isotopically enriched atoms. Compounds having the present structure except for the replacement of a hydrogen atom by a deuterium or tritium, or the replacement of a carbon atom by a $^{13}C$- or $^{14}C$-enriched carbon are within the scope of the invention. For example, deuterium has been widely used to examine the pharmacokinetics and metabolism of biologically active compounds. Although deuterium behaves similarly to hydrogen from a chemical perspective, there are significant differences in bond energies and bond lengths between a deuterium-carbon bond and a hydrogen-carbon bond. Consequently, replacement of hydrogen by deuterium in a biologically active compound may result in a compound that generally retains its biochemical potency and selectivity but manifests significantly different absorption, distribution, metabolism, and/or excretion (ADME) properties compared to its isotope-free counterpart. Thus, deuterium substitution may result in improved drug efficacy, safety, and/or tolerability for some biologically active compounds.

The compounds of the present invention may crystallize in more than one form, a characteristic known as polymorphism, and such polymorphic forms ("polymorphs") are within the scope of the present invention. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be effected by any suitable method known in the art. See, for example, *Stereochemistry of Organic Compounds* (Wiley-Interscience, 1994).

The present invention includes a salt or solvate of the compounds herein described, including combinations thereof such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

II. General Synthetic Methods

The compounds of the present invention can be prepared via the coupling of a mono-protected [3.1.1]heptyl-diazabicycle, namely one in which one of the two amine functional groups is rendered un-reactive by suitable derivatization, with a suitably activated carboxylic acid, chloroformate, or isothionate derivative (Scheme 1).

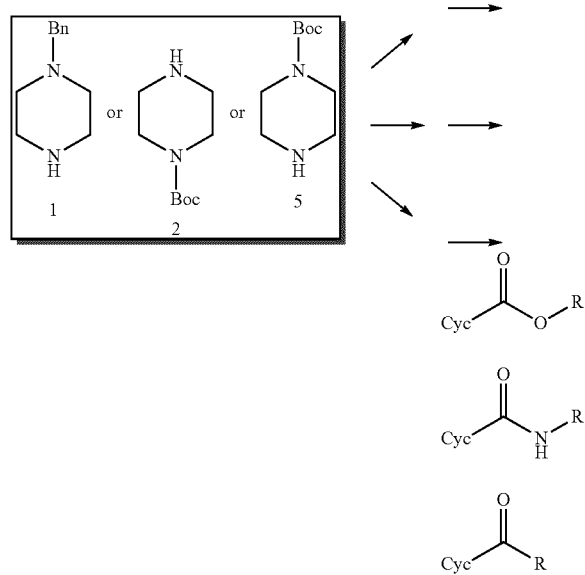

Methods for the preparation of several mono-protected diazabicycles which can be used to prepare the compounds of the present invention (specifically, compounds 1 and 2, Scheme 1) are disclosed in WO 2005/108402 to Pinna, et al. (incorporated by reference with regard to such synthetic teachings). Those skilled in the art of organic synthesis will recognize that other suitably mono-protected diazabicycles (such as compound 5, Scheme 1) can also be used to prepare compound of the present invention (see, for example, T. W. Greene and P. G. M. Wuts, Protective Groups in Organic Synthesis, 3$^{rd}$ Edition, John Wiley & Sons, New York (1999).

One means of making amides of the present invention is to couple a suitable mono N-protected-3,6-diazabicyclo[3.1.1] heptane with a suitably functionalized carboxylic acid, followed by removal of any protecting groups. A wide variety of carboxylic acids are commercially available. The condensation of an amine and a carboxylic acid, to produce an amide, typically requires the use of a suitable activating agent, such as N,N'-dicyclohexylcarbodiimide (DCC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), O-(benzotriazol-1-yl)-N,N,N',N'-bis(tetramethylene)uronium hexafluorophosphate (HBPyU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), or (1-ethyl-3-(3-dimethylaminopropyl)carbodiimide) (EDCI) with 1-hydroxybenzotriazole (HOBt). Other activating agents are well known to those skilled in the art, for example, see Kiso and Yajima, Peptides, pp 39-91, Academic Press, San Diego, Calif. (1995).

Alternatively, amides of the present invention can be prepared by coupling a mono-protected diazabicycle with a suitably functionalized acid chloride, which may be available commercially or may be prepared by conversion of the suitably functionalized carboxylic acid. The acid chloride may be prepared by treatment of the appropriate carboxylic acid with, among other reagents, thionyl chloride or oxalyl chloride.

A similar strategy as described above can be used for the preparation of carbamates and ureas of the present invention. Briefly, carbamates of the present invention can be prepared by coupling a suitable functionalized alkyl-, aryl-, or heteroaryl-chloroformate with a suitable mono N-protected-3,6-diazabicyclo[3.1.1]heptane, followed by removal of any protecting groups. Similarly, a suitable mono N-protected-3,6-diazabicyclo[3.1.1]heptane can be coupled with a suitable functionalized alkyl-, aryl-, or heteroaryl-isocyanate, followed by removal of any protecting groups, to prepare ureas of the present invention.

As will be appreciated by those skilled in the art, the use of certain starting materials containing ancillary reactive functional groups may require additional protection/deprotection steps to prevent interference with the coupling reaction. Such protection/deprotection steps are well known in the art (for example, see T. W. Green and P. G. M. Wuts, Protective Groups in Organic Synthesis, 3$^{rd}$ Edition, John Wiley & Sons, New York (1999)).

As will be appreciated by those skilled in the art throughout the present specification, the number and nature of substituents on rings in the compounds of the present invention will be selected so as to avoid sterically undesirable combinations.

Those skilled in the art of organic synthesis will appreciate that there exist multiple means of producing compounds of the present invention, as well as means for producing compounds of the present invention which are labeled with a radioisotope appropriate to various uses. For example, coupling of a $^{11}$C- or $^{18}$F-labeled acid, chloroformate, or isocyanate with compound a suitable mono N-protected-3,6-diazabicyclo[3.1.1]heptane followed by removal of any protecting groups as described above will produce a compound suitable for use in positron emission tomography. Likewise, coupling of a $^{3}$H- or $^{14}$C-labeled acid, chloroformate, or isocyanate with a suitable mono N-protected-3,6- diazabicyclo[3.1.1]heptane followed by removal of any protecting groups as described above will produce an isotopically modified compound suitable for use in receptor binding and metabolism studies or as an alternative therapeutic compound.

III. Pharmaceutical Compositions

Although it is possible to administer the compound of the present invention in the form of a bulk active chemical, it is preferred to administer the compound in the form of a pharmaceutical composition or formulation. Thus, one aspect the present invention includes pharmaceutical compositions comprising one or more compounds of Formula I and/or pharmaceutically acceptable salts thereof and one or more pharmaceutically acceptable carriers, diluents, or excipients. Another aspect of the invention provides a process for the preparation of a pharmaceutical composition including admixing one or more compounds of Formula I and/or pharmaceutically acceptable salts thereof with one or more pharmaceutically acceptable carriers, diluents or excipients.

The manner in which the compound of the present invention is administered can vary. The compound of the present invention is preferably administered orally. Preferred pharmaceutical compositions for oral administration include tablets, capsules, caplets, syrups, solutions, and suspensions. The pharmaceutical compositions of the present invention may be provided in modified release dosage forms such as time-release tablet and capsule formulations.

The pharmaceutical compositions can also be administered via injection, namely, intravenously, intramuscularly, subcutaneously, intraperitoneally, intraarterially, intrathecally, and intracerebroventricularly. Intravenous administration is a preferred method of injection. Suitable carriers for injection are well known to those of skill in the art and include 5% dextrose solutions, saline, and phosphate buffered saline.

The formulations may also be administered using other means, for example, rectal administration. Formulations useful for rectal administration, such as suppositories, are well known to those of skill in the art. The compounds can also be administered by inhalation, for example, in the form of an aerosol; topically, such as, in lotion form; transdermally, such as, using a transdermal patch (for example, by using technology that is commercially available from Novartis and Alza Corporation); by powder injection; or by buccal, sublingual, or intranasal absorption.

The term "intranasal delivery" or "nasal delivery" as used herein means a method for drug absorption through and within the nose. The term "buccal delivery" as used herein means a method for presenting the drug for absorption through the buccal, including inner cheek, tissue. The term "sublingual delivery" means delivery of the active agent under the tongue. Collectively, these are transmucosal delivery methods.

Drugs can be absorbed through mucosal surfaces, such as those in the nasal passage and in the oral cavity. Drug delivery via mucosal surfaces can be efficient because they lack the stratum corneum of the epidermis, a major barrier to absorption across the skin. Mucosal surfaces are also typically rich in blood supply, which can rapidly transport drugs systemically while avoiding significant degradation by first-pass hepatic metabolism.

There are three routes of absorption for drugs sprayed onto the olfactory mucosa, including by the olfactory neurons, by the supporting cells and surrounding capillary bed, and into the cerebro-spinal fluid. Absorption of drugs through the nasal mucosa tends to be rapid.

Like intranasal administration, oral transmucosal absorption is generally rapid because of the rich vascular supply to the mucosa and the lack of a stratum corneum in the epidermis. Such drug transport typically provides a rapid rise in blood concentrations, and similarly avoids the enterohepatic circulation and immediate destruction by gastric acid or partial first-pass effects of gut wall and hepatic metabolism.

Drugs typically need to have prolonged exposure to an oral mucosal surface for significant drug absorption to occur. Factors affecting drug delivery include taste, which can affect contact time, and drug ionization. Drug absorption is generally greater from the buccal or oral mucosa than from the tongue and gingiva. One limitation associated with buccal drug delivery is low flux, which often results in low drug bioavailability. Low flux may be somewhat offset by using buccal penetration enhancers, as are known in the art, to increase the flux of drugs through the mucosa.

In either of the intranasal or buccal routes, drug absorption can be delayed or prolonged, or uptake may be almost as rapid as if an intravenous bolus were administered. Because of the high permeability of the rich blood supply, the sublingual route can provide a rapid onset of action.

The intranasal, buccal, and sublingual routes can be preferred for use in treating patients who have difficulty in swallowing tablets, capsules, or other oral solids, or those who have disease-compromised intestinal absorption.

Pharmaceutical compositions may be formulated in unit dose form, or in multiple or subunit doses.

The administration of the pharmaceutical compositions described herein can be intermittent, or at a gradual, continuous, constant or controlled rate. The pharmaceutical compositions may be administered to a warm-blooded animal, for example, a mammal such as a mouse, rat, cat, rabbit, dog, pig, cow, or monkey; but advantageously is administered to a human being. In addition, the time of day and the number of times per day that the pharmaceutical composition is administered can vary.

The compounds of the present invention may be used in the treatment of a variety of disorders and conditions and, as such, may be used in combination with a variety of other suitable therapeutic agents useful in the treatment or prophylaxis of those disorders or conditions. Thus, one embodiment of the present invention includes the administration of the compound of the present invention in combination with other therapeutic compounds. For example, the compound of the present invention can be used in combination with other NNR ligands (such as varenicline), allosteric modulators of NNRs, antioxidants (such as free radical scavenging agents), antibacterial agents (such as penicillin antibiotics), antiviral agents (such as nucleoside analogs, like zidovudine and acyclovir), anticoagulants (such as warfarin), anti-inflammatory agents (such as NSAIDs), anti-pyretics, analgesics, anesthetics (such as used in surgery), acetylcholinesterase inhibitors (such as donepezil and galantamine), antipsychotics (such as haloperidol, clozapine, olanzapine, and quetiapine), immuno-suppressants (such as cyclosporin and methotrexate), neuroprotective agents, steroids (such as steroid hormones), corticosteroids (such as dexamethasone, predisone, and hydrocortisone), vitamins, minerals, nutraceuticals, anti-depressants (such as imipramine, fluoxetine, paroxetine, escitalopram, sertraline, venlafaxine, and duloxetine), anxiolytics (such as alprazolam and buspirone), anticonvulsants (such as phenyloin and gabapentin), vasodilators (such as prazosin and sildenafil), mood stabilizers (such as valproate and aripiprazole), anti-cancer drugs (such as anti-proliferatives), anti-hypertensive agents (such as atenolol, clonidine, amlopidine, verapamil, and olmesartan), laxatives, stool softeners, diuretics (such as furosemide), anti-spasmotics (such as dicyclomine), anti-dyskinetic agents, and anti-ulcer medications (such as esomeprazole). Such a combination of pharmaceutically active agents may be administered together or separately and, when administered separately, administration may occur simultaneously or sequentially, in any order. The amounts of the compounds or agents and the relative timings of administration will be selected in order to achieve the desired therapeutic effect. The administration in combination of a compound of the present invention with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second. Such sequential administration may be close in time or remote in time.

Another aspect of the present invention includes combination therapy comprising administering to the subject a therapeutically or prophylactically effective amount of the compound of the present invention and one or more other therapy including chemotherapy, radiation therapy, gene therapy, or immunotherapy.

IV. Methods of Using

The compounds of the present invention can be used for the prevention or treatment of various conditions or disorders for which other types of nicotinic compounds have been proposed or are shown to be useful as therapeutics, such as CNS disorders, inflammation, inflammatory response associated with bacterial and/or viral infection, pain, diabetes, metabolic syndrome, autoimmune disorders, dermatological conditions, addictions, obesity or other disorders described in further detail herein. This compound can also be used as a diagnostic agent in receptor binding studies (in vitro and in vivo). Such therapeutic and other teachings are described, for example, in references previously listed herein, including Williams et al., *Drug News Perspec.* 7(4): 205 (1994), Arneric et al., *CNS Drug Rev.* 1(1): 1-26 (1995), Arneric et al., *Exp. Opin. Invest. Drugs* 5(1): 79-100 (1996), Yang et al., *Acta Pharmacol. Sin.* 30(6): 740-751 (2009), Bencherif et al., *J. Pharmacol. Exp. Ther.* 279: 1413 (1996), Lippiello et al., *J. Pharmacol. Exp. Ther.* 279: 1422 (1996), Damaj et al., *J. Pharmacol. Exp. Ther.* 291: 390 (1999); Chiari et al., *Anesthesiology* 91: 1447 (1999), Lavand'homme and Eisenbach, *Anesthesiology* 91: 1455 (1999), Holladay et al., *J. Med. Chem.* 40(28): 4169-94 (1997), Bannon et al., *Science* 279: 77 (1998), PCT WO 94/08992, PCT WO 96/31475, PCT WO 96/40682, and U.S. Pat. Nos. 5,583,140 to Bencherif et al., 5,597,919 to Dull et al., 5,604,231 to Smith et al. and 5,852,041 to Cosford et al.

CNS Disorders

The compounds and their pharmaceutical compositions are useful in the treatment or prevention of a variety of CNS disorders, including neurodegenerative disorders, neuropsychiatric disorders, neurologic disorders, and addictions. The compounds and their pharmaceutical compositions can be used to treat or prevent cognitive deficits and dysfunctions, age-related and otherwise; attentional disorders and dementias, including those due to infectious agents or metabolic disturbances; to provide neuroprotection; to treat convulsions and multiple cerebral infarcts; to treat mood disorders, compulsions and addictive behaviors; to provide analgesia; to control inflammation, such as mediated by cytokines and nuclear factor kappa B; to treat inflammatory disorders; to provide pain relief; and to treat infections, as anti-infectious agents for treating bacterial, fungal, and viral infections. Among the disorders, diseases and conditions that the compounds and pharmaceutical compositions of the present invention can be used to treat or prevent are: age-associated memory impairment (AAMI), mild cognitive impairment (MCI), age-related cognitive decline (ARCD), pre-senile dementia, early onset Alzheimer's disease, senile dementia, dementia of the Alzheimer's type, Alzheimer's disease, cognitive impairment no dementia (CIND), Lewy body dementia, HIV-dementia, AIDS dementia complex, vascular dementia, Down syndrome, head trauma, traumatic brain injury (TBI), dementia pugilistica, Creutzfeld-Jacob Disease and prion diseases, stroke, central ischemia, peripheral ischemia, attention deficit disorder, attention deficit hyperactivity disorder, dyslexia, schizophrenia, schizophreniform disorder, schizoaffective disorder, cognitive dysfunction in schizophrenia, cognitive deficits in schizophrenia, Parkinsonism including Parkinson's disease, postencephalitic parkinsonism, parkinsonism-dementia of Gaum, frontotemporal dementia Parkinson's Type (FTDP), Pick's disease, Niemann-Pick's Disease, Huntington's Disease, Huntington's chorea, dyskinesias, L-dopa induced dyskinesia, tardive dyskinesia, spastic dystonia, hyperkinesia, progressive supranuclear palsy, progressive supranuclear paresis, restless leg syndrome, Creutzfeld-Jakob disease, multiple sclerosis, amyotrophic lateral sclerosis (ALS), motor neuron diseases (MND), multiple system atrophy (MSA), corticobasal degeneration, Guillain-Barré Syndrome (GBS), and chronic inflammatory demyelinating polyneuropathy (CIDP), epilepsy, autosomal dominant nocturnal frontal lobe epilepsy, mania, anxiety, depression, premenstrual dysphoria, panic disorders, bulimia, anorexia, narcolepsy, excessive daytime sleepiness, bipolar disorders, generalized anxiety disorder, obsessive compulsive disorder, rage outbursts, conduct disorder, oppositional defiant disorder, Tourette's syndrome, autism, drug and alcohol addiction, tobacco addiction, compulsive overeating and sexual dysfunction.

Cognitive impairments or dysfunctions may be associated with psychiatric disorders or conditions, such as schizophrenia and other psychotic disorders, including but not limited to psychotic disorder, schizophreniform disorder, schizoaffective disorder, delusional disorder, brief psychotic disorder, shared psychotic disorder, and psychotic disorders due to a general medical conditions, dementias and other cognitive disorders, including but not limited to mild cognitive impairment, pre-senile dementia, Alzheimer's disease, senile dementia, dementia of the Alzheimer's type, age-related memory impairment, Lewy body dementia, vascular dementia, AIDS dementia complex, dyslexia, Parkinsonism including Parkinson's disease, cognitive impairment and dementia of Parkinson's Disease, cognitive impairment of multiple sclerosis, cognitive impairment caused by traumatic brain injury, dementias due to other general medical conditions, anxiety disorders, including but not limited to panic disorder without agoraphobia, panic disorder with agoraphobia, agoraphobia without history of panic disorder, specific phobia, social phobia, obsessive-compulsive disorder, post-traumatic stress disorder, acute stress disorder, generalized anxiety disorder and generalized anxiety disorder due to a general medical condition, mood disorders, including but not limited to major depressive disorder, dysthymic disorder, bipolar depression, bipolar mania, bipolar I disorder, depression associated with manic, depressive or mixed episodes, bipolar II disorder, cyclothymic disorder, and mood disorders due to general medical conditions, sleep disorders, including but not limited to dyssomnia disorders, primary insomnia, primary hypersomnia, narcolepsy, parasomnia disorders, nightmare disorder, sleep terror disorder and sleepwalking disorder, mental retardation, learning disorders, motor skills disorders, communication disorders, pervasive developmental disorders, attention-deficit and disruptive behavior disorders, attention deficit disorder, attention deficit hyperactivity disorder, feeding and eating disorders of infancy, childhood, or adults, tic disorders, elimination disorders, substance-related disorders, including but not limited to substance dependence, substance abuse, substance intoxication, substance withdrawal, alcohol-related disorders, amphetamine or amphetamine-like-related disorders, caffeine-related disorders, cannabis-related disorders, cocaine-related disorders, hallucinogen-related disorders, inhalant-related disorders, nicotine-related disorders, opioid-related disorders, phencyclidine or phencyclidine-like-related disorders, and sedative-, hypnotic- or anxiolytic-related disorders, personality disorders, including but not limited to obsessive-compulsive personality disorder and impulse-control disorders. Cognitive performance may be assessed with a validated cognitive scale, such as, for example, the cognitive subscale of the Alzheimer's Disease Assessment Scale (ADAS-cog). One measure of the effectiveness of the compounds of the present invention in improving cognition may include measuring a patient's degree of change according to such a scale.

Regarding compulsions and addictive behaviors, the compounds of the present invention may be used as a therapy for nicotine addiction and for other brain-reward disorders, such as substance abuse including alcohol addiction, illicit and prescription drug addiction, eating disorders, including obesity, and behavioral addictions, such as gambling, or other similar behavioral manifestations of addiction.

The above conditions and disorders are discussed in further detail, for example, in the American Psychiatric Association: Diagnostic and Statistical Manual of Mental Disorders, Fourth Edition, Text Revision, Washington, D.C., American Psychiatric Association, 2000. This Manual may also be referred to for greater detail on the symptoms and diagnostic features associated with substance use, abuse, and dependence.

Preferably, the treatment or prevention of diseases, disorders and conditions occurs without appreciable adverse side effects, including, for example, significant increases in blood pressure and heart rate, significant negative effects upon the gastro-intestinal tract, and significant effects upon skeletal muscle.

The compounds of the present invention, when employed in effective amounts, are believed to modulate the activity of the α4β2 and/or α6-containing NNRs without appreciable interaction with the nicotinic subtypes that characterize the human ganglia, as demonstrated by a lack of the ability to elicit nicotinic function in adrenal chromaffin tissue, or skeletal muscle, further demonstrated by a lack of the ability to elicit nicotinic function in cell preparations expressing muscle-type nicotinic receptors. Thus, these compounds are believed capable of treating or preventing diseases, disorders and conditions without eliciting significant side effects associated activity at ganglionic and neuromuscular sites. Thus, administration of the compounds is believed to provide a therapeutic window in which treatment of certain diseases, disorders and conditions is provided, and certain side effects are avoided. That is, an effective dose of the compound is believed sufficient to provide the desired effects upon the disease, disorder or condition, but is believed insufficient, namely is not at a high enough level, to provide undesirable side effects.

Thus, the present invention provides the use of a compound of the present invention, or a pharmaceutically acceptable salt thereof, for use in therapy, such as a therapy described above.

In yet another aspect the present invention provides the use of a compound of the present invention, or a pharmaceutically acceptable salt thereof, in the manufacture of a medicament for use in the treatment of a CNS disorder, such as a disorder, disease or condition described hereinabove.

Inflammation

The nervous system, primarily through the vagus nerve, is known to regulate the magnitude of the innate immune response by inhibiting the release of macrophage tumor necrosis factor (TNF). This physiological mechanism is known as the "cholinergic anti-inflammatory pathway" (see, for example, Tracey, "The Inflammatory Reflex," *Nature* 420: 853-9 (2002)). Excessive inflammation and tumor necrosis factor synthesis cause morbidity and even mortality in a variety of diseases. These diseases include, but are not limited to, endotoxemia, rheumatoid arthritis, osteoarthritis, psoriasis, asthma, atherosclerosis, idiopathic pulmonary fibrosis, and inflammatory bowel disease.

Inflammatory conditions that can be treated or prevented by administering the compounds described herein include, but are not limited to, chronic and acute inflammation, psoriasis, endotoxemia, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, irritable bowel syndrome, Crohn's disease, ulcers, ulcerative colitis, acute cholangitis, aphthous stomatitis, cachexia, pouchitis, glomerulonephritis, lupus nephritis, thrombosis, and graft vs. host reaction.

Inflammatory Response Associated with Bacterial and/or Viral Infection

Many bacterial and/or viral infections are associated with side effects brought on by the formation of toxins, and the body's natural response to the bacteria or virus and/or the toxins. As discussed above, the body's response to infection often involves generating a significant amount of TNF and/or other cytokines. The over-expression of these cytokines can result in significant injury, such as septic shock (when the bacteria is sepsis), endotoxic shock, urosepsis, viral pneumonitis and toxic shock syndrome.

Cytokine expression is mediated by NNRs, and can be inhibited by administering agonists or partial agonists of these receptors. Those compounds described herein that are agonists or partial agonists of these receptors can therefore be used to minimize the inflammatory response associated with bacterial infection, as well as viral and fungal infections. Examples of such bacterial infections include anthrax, botulism, and sepsis. Some of these compounds may also have antimicrobial properties.

These compounds can also be used as adjunct therapy in combination with existing therapies to manage bacterial, viral and fungal infections, such as antibiotics, antivirals and antifungals. Antitoxins can also be used to bind to toxins produced by the infectious agents and allow the bound toxins to pass through the body without generating an inflammatory response. Examples of antitoxins are disclosed, for example, in U.S. Pat. No. 6,310,043 to Bundle et al. Other agents effective against bacterial and other toxins can be effective and their therapeutic effect can be complemented by co-administration with the compounds described herein.

Pain

The compounds can be administered to treat and/or prevent pain, including acute, neurologic, inflammatory, neuropathic and chronic pain. The compounds can be used in conjunction with opiates to minimize the likelihood of opiate addiction (e.g., morphine sparing therapy). The analgesic activity of compounds described herein can be demonstrated in models of persistent inflammatory pain and of neuropathic pain, performed as described in U.S. Published Patent Application No. 20010056084 A1 (Allgeier et al.) (e.g., mechanical hyperalgesia in the complete Freund's adjuvant rat model of inflammatory pain and mechanical hyperalgesia in the mouse partial sciatic nerve ligation model of neuropathic pain).

The analgesic effect is suitable for treating pain of various genesis or etiology, in particular in treating inflammatory pain and associated hyperalgesia, neuropathic pain and associated hyperalgesia, chronic pain (e.g., severe chronic pain, postoperative pain and pain associated with various conditions including cancer, angina, renal or biliary colic, menstruation, migraine, and gout). Inflammatory pain may be of diverse genesis, including arthritis and rheumatoid disease, tenosynovitis and vasculitis. Neuropathic pain includes trigeminal or herpetic neuralgia, neuropathies such as diabetic neuropathy pain, causalgia, low back pain and deafferentation syndromes such as brachial plexus avulsion.

Other Disorders

In addition to treating CNS disorders, inflammation, and neovascularization, and pain, the compounds of the present invention can be also used to prevent or treat certain other conditions, diseases, and disorders in which NNRs play a role. Examples include autoimmune disorders such as lupus, disorders associated with cytokine release, cachexia secondary to infection (e.g., as occurs in AIDS, AIDS related complex and neoplasia), obesity, pemphitis, urinary incontinence, overactive bladder, diarrhea, constipation, retinal diseases, infectious diseases, myasthenia, Eaton-Lambert syndrome, hypertension, preeclampsia, osteoporosis, vasoconstriction, vasodilatation, cardiac arrhythmias, type I diabetes, type II diabetes, bulimia, anorexia and sexual dysfunction, as well as those indications set forth in published PCT application WO 98/25619. The compounds of this invention can also be administered to treat convulsions such as those that are symptomatic of epilepsy, and to treat conditions such as syphillis and Creutzfeld-Jakob disease. Lastly, the compounds of this invention may be used to treat a variety of dermatological disorders, including but not limited to psoriasis, dermatitis, acne, pustulosis, vitilago, and the like.

Diagnostic Uses

The compounds can be used in diagnostic compositions, such as probes, particularly when they are modified to include appropriate labels. The probes can be used, for example, to determine the relative number and/or function of specific receptors, particularly the α4β2 and/or α6-containing receptor subtypes. For this purpose the compounds of the present invention most preferably are labeled with a radioactive isotopic moiety such as $^{11}C$, $^{18}F$, $^{76}Br$, $^{123}I$ or $^{125}I$.

The administered compounds can be detected using known detection methods appropriate for the label used. Examples of detection methods include position emission topography (PET) and single-photon emission computed tomography (SPECT). The radiolabels described above are useful in PET (e.g., $^{11}C$, $^{18}F$ or $^{76}Br$) and SPECT (e.g., $^{123}I$) imaging, with half-lives of about 20.4 minutes for $^{11}C$, about 109 minutes for $^{18}F$, about 13 hours for $^{123}I$, and about 16 hours for $^{76}Br$. A high specific activity is desired to visualize the selected receptor subtypes at non-saturating concentrations. The administered doses typically are below the toxic range and provide high contrast images. The compounds are expected to be capable of administration in non-toxic levels. Determination of dose is carried out in a manner known to one skilled in the art of radiolabel imaging. See, for example, U.S. Pat. No. 5,969,144 to London et al.

The compounds can be administered using known techniques. See, for example, U.S. Pat. No. 5,969,144 to London et al., as noted. The compounds can be administered in formulation compositions that incorporate other ingredients, such as those types of ingredients that are useful in formulating a diagnostic composition. Compounds useful in accordance with carrying out the present invention most preferably are employed in forms of high purity. See, U.S. Pat. No. 5,853,696 to Elmalch et al.

After the compounds are administered to a subject (e.g., a human subject), the presence of that compound within the subject can be imaged and quantified by appropriate techniques in order to indicate the presence, quantity, and functionality of selected NNR subtypes. In addition to humans, the compounds can also be administered to animals, such as mice, rats, dogs, and monkeys. SPECT and PET imaging can be carried out using any appropriate technique and apparatus. See Villemagne et al., In: Arneric et al. (Eds.) *Neuronal Nicotinic Receptors: Pharmacology and Therapeutic Opportunities*, 235-250 (1998) and U.S. Pat. No. 5,853,696 to Elmalch et al., each herein incorporated by reference, for a disclosure of representative imaging techniques.

The radiolabeled compounds bind with high affinity to selective NNR subtypes (e.g., α4β2 and/or α6-containing) and preferably exhibit negligible non-specific binding to other nicotinic cholinergic receptor subtypes (e.g., those receptor subtypes associated with muscle and ganglia). As such, the compounds can be used as agents for noninvasive imaging of nicotinic cholinergic receptor subtypes within the body of a subject, particularly within the brain for diagnosis associated with a variety of CNS diseases and disorders.

In one aspect, the diagnostic compositions can be used in a method to diagnose disease in a subject, such as a human patient. The method involves administering to that patient a detectably labeled compound as described herein, and detecting the binding of that compound to selected NNR subtypes (e.g., α4β2 and/or α6-containing receptor subtypes). Those skilled in the art of using diagnostic tools, such as PET and SPECT, can use the radiolabeled compounds described herein to diagnose a wide variety of conditions and disorders, including conditions and disorders associated with dysfunction of the central and autonomic nervous systems. Such disorders include a wide variety of CNS diseases and disorders, including Alzheimer's disease, Parkinson's disease, and schizophrenia. These and other representative diseases and disorders that can be evaluated include those that are set forth in U.S. Pat. No. 5,952,339 to Bencherif et al.

In another aspect, the diagnostic compositions can be used in a method to monitor selective nicotinic receptor subtypes of a subject, such as a human patient. The method involves administering a detectably labeled compound as described herein to that patient and detecting the binding of that compound to selected nicotinic receptor subtypes namely, the α4β2 and/or α6-containing receptor subtypes.

Receptor Binding

The compounds of this invention can be used as reference ligands in binding assays for compounds which bind to NNR subtypes, particularly the and/or α6-containing receptor subtypes. For this purpose the compounds of this invention are preferably labeled with a radioactive isotopic moiety such as $^3H$, or $^{14}C$. Examples of such binding assays are described in detail below.

V. Synthetic Examples

Example 1

3-benzyl-3,6-diazabicyclo[3.1.1]heptane (1)

3-benzyl-3,6-diazabicyclo[3.1.1]heptane (1) was prepared according to the procedure of WO 2005/108402 to Pinna, et al.

Example 2

6-(tert-butoxycarbonyl)-3,6-diazabicyclo[3.1.1]heptane (2)

6-(tert-butoxycarbonyl)-3,6-diazabicyclo[3.1.1]heptane (2) was prepared according to the procedure of WO 2005/108402 to Pinna, et al

Example 3

3-benzyl-6-(trifluoromethylcarbonyl)-3,6-diazabicyclo[3.1.1]heptane (3)

To a solution of 3-benzyl-3,6-diazabicyclo[3.1.1]heptane (1) (7.5 g, 39.8 mmol), methanol (300 mL), and triethylamine (6.70 mL, 1.2 eq, 47.8 mmol) at 0° C. was added trifluoroacetic anhydride (6.7 mL, 1.2 eq, 47.80 mmol). The solution was stirred at ambient temperature for 4 h and the solvent was removed under vacuum. The solids were filtered off and washed with methylene chloride. The solvent was removed in vacuo and the residue purified by column chromatography using a 0-100% ethyl acetate in hexanes gradient. The appropriate fractions were collected, pooled, and evaporated to give 3-benzyl-6-(trifluoromethylcarbonyl)-3,6-diazabicyclo[3.1.1]heptane (3) (7.0 g, 62% yield) as a yellow solid.

Example 4

3-(tert-butoxycarbonyl)-6-(trifluoromethylcarbonyl)-3,6-diazabicyclo[3.1.1]heptane (4)

A solution of 3-benzyl-6-(trifluoromethylcarbonyl)-3,6-diazabicyclo[3.1.1]heptane (3) (8.3 g, 29.2 mmol), ethanol (60 mL), di-t-butyldicarbonate (6.4 g, 29.2 mmol) and 10% palladium on carbon (3.2 g, 30.1 mmol) in a Parr reactor was shaken at 60° C. under 3 atm of hydrogen for 16 h. The solution was cooled, filtered through diatomaceous earth, and washed with methanol. The solvent was evaporated under reduced pressure and the remaining residue washed with methylene chloride and saturated ammonium chloride solution. The organic layer was passed through a phase separator and purified by column chromatography eluting with a 0-50% ethyl acetate in hexanes gradient. The appropriate fractions were collected, pooled, and evaporated to give 3-(tert-butoxycarbonyl)-6-(trifluoromethylcarbonyl)-3,6-diazabicyclo[3.1.1]heptane (4) (8.5 g, 99% yield).

Example 5

3-(tert-butoxycarbonyl)-3,6-diazabicyclo[3.1.1]heptane (5)

A solution of 3-(tert-butoxycarbonyl)-6-(trifluoromethylcarbonyl)-3,6-diazabicyclo[3.1.1]heptane (4) (8.5 g, 28.9 mmol) and potassium carbonate (30.7 g, 2 eq, 57.8 mmol) in methanol (150 mL) was heated at 70° C. for 3 h. The solution was cooled to ambient temperature and the solvent was removed in vacuo. The crude material was dissolved in a 1:1 solution of methylene chloride:methanol and filtered to give 3-(tert-butoxycarbonyl)-3,6-diazabicyclo[3.1.1]heptane (5) (4.5 g, 79% yield) as an off-white solid.

Example 6

3-(cyclopropylcarbonyl)-3,6-diazabicyclo[3.1.1]heptane (6)

A solution of 6-(tert-butoxycarbonyl)-3,6-diazabicyclo[3.1.1]heptane (2) (2.50 g, 12.6 mmol), cyclopropanecarboxylic acid (1.2 mL, 1.2 eq, 15 mmol), triethylamine (3.50 mL, 25.2 mmol), dichloromethane (100 mL) and O-benzotriazol-1-yl-tetramethyluronium hexafluorophosphate (9.6 g, 2 eq, 25 mmol) was stirred at ambient temperature for 2 h. Saturated ammonium chloride (50 mL) was added and the reaction mixture was left to stir for 30 min. The mixture was then passed through a phase extractor (Isolute from Biotage) and the solvent was removed in vacuo.

The crude mixture was dissolved in 20 mL of methylene chloride. Trifluoroacetic acid (5 mL) was added and the reaction was stirred for 16 h. The solvent was removed in vacuo and the residue was dissolved in 1 mL of 1:1 methylene chloride:methanol and passed through a SCX-2 column (Biotage) (eluting with 3 mL 1:1 methylene chloride:methanol, then 7N methanolic ammonia). The crude product was purified on a silica gel column eluting with a chloroform to 90:9:1 Chloroform:methanol:ammonium hydroxide gradient over 12 column volumes. Appropriate fractions were collected and solvent was removed in vacuo to yield 3-(cyclopropylcarbonyl)-3,6-diazabicyclo[3.1.1]heptane (6) (750 mg; 36% yield) as a yellow oil.

Example 7

3-(propoxycarbonyl)-3,6-diazabicyclo[3.1.1]heptane (7)

To a solution of 6-(tert-butoxycarbonyl)-3,6-diazabicyclo[3.1.1]heptane (2) (50 mg, 0.25 mmol) in 5 mL of methylene chloride was added triethylamine (67 µL, 0.5 mmol) and the solution was cooled to 0° C. Propyl chloroformate (31 µL, 27.5 mmol) was added and the solution was stirred for 1 h. The solvent was removed in vacuo and the residue was washed with 50 mM sodium acetate in methylene chloride solution. The solution was stirred 10 min and passed through a phase separator. The solvent was removed in vacuo to give crude 3-(propoxycarbonyl)-6-(tert-butoxycarbonyl)-3,6-diazabicyclo[3.1.1]heptane.

The crude mixture was dissolved in 3 mL of methylene chloride. Trifluoroacetic acid (3 mL) was added and the reaction was stirred for 2 h. The solvent was removed in vacuo at 40° C. and the residue was dissolved in 1:1 methylene chloride:methanol and passed through a SCX-2 column (Biotage) (eluting with 2 mL 1:1 methylene chloride:methanol, then 7N methanolic ammonia). The crude product was purified on a silica gel column eluting with a chloroform to 90:9:1 Chloroform:methanol:ammonium hydroxide gradient. Appropriate fractions were collected and solvent was removed in vacuo to yield 3-(propoxycarbonyl)-3,6-diazabicyclo[3.1.1]heptane (7) (12 mg, 26%) as a clear oil.

Example 8

3-(methoxyethoxycarbonyl)-3,6-diazabicyclo[3.1.1]heptane (8)

To a solution of 6-(tert-butoxycarbonyl)-3,6-diazabicyclo[3.1.1]heptane (2) (50 mg, 0.25 mmol) in 5 mL of methylene chloride was added triethylamine (67 µL, 0.5 mmol) and the solution was cooled to 0° C. Methoxyethyl chloroformate (32 µL, 27.5 mmol) was added and the solution was stirred for 1 h. The solvent was removed in vacuo and the residue was washed with 50 mM sodium acetate in methylene chloride solution. The solution was stirred 10 min and passed through a phase separator. The solvent was removed in vacuo to give crude 3-(methoxyethoxycarbonyl)-6-(tert-butoxycarbonyl)-3,6-diazabicyclo[3.1.1]heptane.

The crude mixture was dissolved in 3 mL of methylene chloride. Trifluoroacetic acid (3 mL) was added and the reaction was stirred for 2 h. The solvent was removed in vacuo at 40° C. and the residue was dissolved in 1:1 methylene chloride:methanol and passed through a SCX-2 column (Biotage) (eluting with 2 mL 1:1 methylene chloride:methanol, then 7N methanolic ammonia). The crude product was purified on a silica gel column eluting with a chloroform to 90:9:1 Chloroform:methanol:ammonium hydroxide gradient. Appropriate fractions were collected and solvent was removed in vacuo to yield 3-(methoxyethoxycarbonyl)-3,6-diazabicyclo[3.1.1]heptane (8) (15 mg, 27%) as a clear oil.

VI. Biological Assays

Example 9

Characterization of Interactions at Nicotinic Acetylcholine Receptors

Cell Lines

SH-EP1/human α4β2 (Eaton et al., 2003), SH-EP1/human α4β4 (Gentry et al., 2003), SH-EP1/α6β3β4α5 (Grinevich et al., 2005), TE671/RD and SH-SY5Y cell lines (obtained from Dr. Ron Lukas, Barrow Neurological Institute, St. Joseph's Hospital and Medical Center, Phoenix, Ariz.) were maintained in proliferative growth phase in Dulbecco's modified Eagle's medium (Gibco/BRL) with 10% horse serum (Gibco BRL), 5% fetal bovine serum (HyClone, Logan Utah), 1 mM sodium pyruvate, 4 mM L-glutamine. For maintenance of stable transfectants, the α4β2 and α4β4 cell media was supplemented with 0.25 mg/mL zeocin and 0.13 mg/mL hygromycin B. Selection was maintained for the α6β3β4α5 cells with 0.25 mg/mL of zeocin, 0.13 mg/mL of hygromycin B, 0.4 mg/mL of geneticin, and 0.2 mg/mL of blasticidin. HEK/human α7/RIC3 cells (obtained from J. Lindstrom, U. Pennsylvania, Philadelphia, Pa.) were maintained in proliferative growth phase in Dulbecco's modified Eagle's medium (Gibco/BRL) with 10% fetal bovine serum (HyClone, Logan Utah), 1 mM sodium pyruvate, 4 mM L-glutamine, 0.4 mg/mL geneticin; 0.2 mg/ml hygromycin B.

Receptor Binding Assays

Preparation of membranes from rat tissues. Rat cortices were obtained from Analytical Biological Services, Incorporated (ABS, Wilmington, Del.). Tissues were dissected from female Sprague-Dawley rats, frozen and shipped on dry ice. Tissues were stored at −20° C. until needed for membrane preparation. Cortices from 10 rats were pooled and homogenized by Polytron (Kinematica GmbH, Switzerland) in 10 volumes (weight:volume) of ice-cold preparative buffer (KCl, 11 mM; $KH_2PO_4$, 6 mM; NaCl 137 mM; $Na_2HPO_4$ 8 mM; HEPES (free acid), 20 mM; iodoacetamide, 5 mM; EDTA, 1.5 mM; 0.1 mM PMSF pH 7.4). The resulting homogenate was centrifuged at 40,000 g for 20 minutes at 4° C. and the resulting pellet was resuspended in 20 volumes of ice-cold water. After 60-minute incubation at 4° C., a new pellet was collected by centrifugation at 40,000 g for 20 minutes at 4° C. The final pellet was resuspended in preparative buffer and stored at −20° C. On the day of the assay, tissue was thawed, centrifuged at 40,000 g for 20 minutes and then resuspended in PBS (Dulbecco's Phosphate Buffered Saline, Life Technologies, pH 7.4) to a final concentration of 2-3 mg protein/mL. Protein concentrations were determined using the Pierce BCA Protein Assay kit (Pierce Biotechnology, Rockford, Ill.), with bovine serum albumin as the standard.

Preparation of membranes from clonal cell lines. Cells were harvested in ice-cold PBS, pH 7.4, then homogenized with a polytron (Brinkmann Instruments, Westbury, N.Y.). Homongenates were centrifuged at 40,000 g for 20 minutes (4° C.). The pellet was resuspended in PBS and protein concentration determined using the Pierce BCA Protein Assay kit (Pierce Biotechnology, Rockford, Ill.).

Competition binding to receptors in membrane preparations. Binding to nicotinic receptors was assayed on membranes using standard methods adapted from published procedures (Lippiello and Fernandes, 1986; Davies et al., 1999). In brief, membranes were reconstituted from frozen stocks (approximately 0.2 mg protein) and incubated for 2 h on ice in 150 ml assay buffer (PBS) in the presence of competitor compound (0.001 nM to 100 mM) and radioligand. $[^3H]$-nicotine (L-(−)-[N-methyl-3H]-nicotine, 69.5 Ci/mmol, Perkin-Elmer Life Sciences) was used for human α4β2 binding studies. $[^3H]$-epibatidine (52 Ci/mmol, Perkin-Elmer Life Sciences) was used for binding studies at the other receptor subtypes. Incubation was terminated by rapid filtration on a multimanifold tissue harvester (Brandel, Gaithersburg, Md.) using GF/B filters presoaked in 0.33% polyethyleneimine (w/v) to reduce non-specific binding. Filters were washed 3 times and the radioactivity retained was determined by liquid scintillation counting.

Binding data analysis. Binding data were expressed as percent total control binding. Replicates for each point were averaged and plotted against the log of drug concentration. The $IC_{50}$ (concentration of the compound that produces 50% inhibition of binding) was determined by least squares non-linear regression using GraphPad Prism software (GraphPAD, San Diego, Calif.). $K_i$ was calculated using the Cheng-Prusoff equation (Cheng and Prusoff, 1973).

Example 10

Tabular Spectral and Receptor Binding Data

The above illustrated amide coupling procedures were used as a basis to make the compounds shown in Table 1. Reagents and conditions will be readily apparent to those skilled in the art. In some cases, compounds were characterized by nuclear magnetic resonance (NMR) data (included in Table 1). In other cases, compounds were structurally characterized by LCMS (included in Table 2).

TABLE 1

| STRUCTURE | LCMS (m/z) | ¹H NMR |
| --- | --- | --- |
| (N-acetyl-3,6-diazabicyclo structure) | 141 | ¹H NMR (400 MHz, CDCl₃): δ 3.81-3.58 (m, 6H), 2.76 (m, 1H), 2.12 (2, 3H), 1.50 (d, J = 8.9 Hz, 1H) |
| (N-isobutyryl structure) | 169 | ¹H NMR (400 MHz, CDCl₃): δ 3.82 (m, 6H), 2.82 (m, 2H), 1.76 (m, 1H), 1.20 (s, 6H) |
| (N-cyclopropanecarbonyl structure) Compound A | 167 | ¹H NMR (400 MHz, CDCl₃): δ 3.82 (m, 4H), 3.65 (m, 2H), 2.62 (m, 1H), 1.72 (m, 1H), 1.46 (m, 1H), 1.00 (m, 2H), 0.72 (m, 2H) |
| (N-propoxycarbonyl structure) | 185 | ¹H NMR (400 MHz, CDCl₃): δ 4.20 (m, 2H), 3.84-3.62 (m, 6H), 2.70 (m, 1H), 1.65 (m, 2H), 1.50 (m, 1H), 0.98 (d, 3H) |
| (N-isopropoxycarbonyl structure) | 185 | ¹H NMR (400 MHz, CDCl₃): δ 5.00 (m, 1H), 3.80-58 (m, 6H), 2.70 (m, 1H), 1.50 (m, 1H), 1.25 (m, 6H) |
| (5-bromofuran-2-carbonyl structure) | 273 | ¹H NMR (400 MHz, CDCl₃): δ 7.12 (s, 1H), 6.47 (s, 1H), 4.20-4.12 (m, 2H), 3.97-3.78 (m, 4H), 2.80 (m, 1H), 1.61 (m, 1H) |
| (3-chlorofuran-2-carbonyl structure) | 260 | ¹H NMR (400 MHz, CDCl₃): δ 7.48 (s, 1H), 6.53 (s, 1H), 4.12-3.82 (m, 4H), 2.84 (m, 1H), 1.61 (d, J = 9.6 Hz, 1H) |

TABLE 1-continued
| STRUCTURE | LCMS (m/z) | ¹H NMR |
|---|---|---|
| 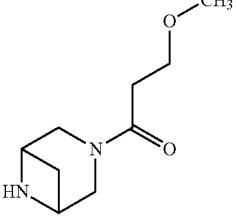 | 185 | ¹H NMR (400 MHz, CDCl₃): δ 3.80-3.76 (m, 8H), 3.36(s, 3H), 2.74 (m, 1H), 2.64 (m, 2H), 1.48 (d, J = 9.2 Hz, 1H) |
| 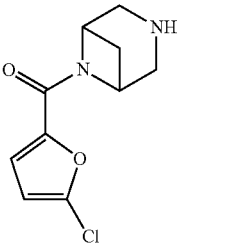 [SMILES: O=C(c1ccc(Cl)o1)N1C2CNCC1C2] | 227 | ¹H NMR (400 MHz, CDCl₃): δ 7.16 (s, 1H), 6.35 (s, 1H), 4.22 (m, 2H), 4.02 (m, 4H), 2.82 (m, 1H), 1.60 (d, J = 9.0 Hz, 1H) |
| 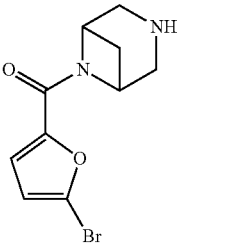 [SMILES: O=C(c1ccc(Br)o1)N1C2CNCC1C2] | 273 | ¹H NMR (400 MHz, CDCl₃): δ 7.10 (s, 1H), 6.45 (s, 1H), 4.22 (m, 2H), 3.98-3.78 (m, 4H), 2.80 (m, 1H), 1.58 (d, J = 9.1 Hz, 1H) |
| 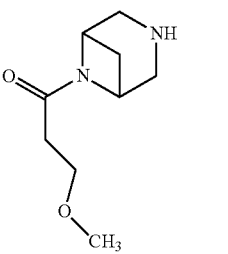 | 185 | ¹H NMR (400 MHz, CDCl₃): δ 3.92-3.72 (m, 8H), 2.74 (m, 1H), 3.36 (s, 3H), 2.70-2.62 (m, 2H), 1.52 (d, J = 9.0 Hz, 1H) |
| 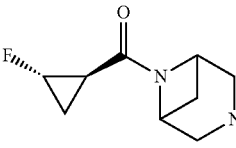 | 185 | ¹H NMR (400 MHz, CD₃OD): δ 4.85 (m, 1H), 4.55 (m, 2H), 4.40 (m, 2H), 4.02 (m, 2H), 3.12 (m, 1H), 2.52 (m, 1H), 1.98 (m, 1H), 1.60 (m, 1H), 1.38 (m, 1H) |
| 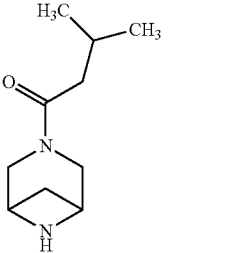 | 183 | ¹H NMR (400 MHz, CD₃OD): δ 4.43 (d, 2H), 4.1 (d, 2H), 4.0 (d, 1H), 3.85 (d, 1H), 2.98 (m, 1H), 2.15-2.40 (m, 3H), 1.86 (d, 1H), 1.0 (d, 6H) |
| 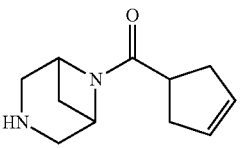 | 193 | ¹H NMR (400 MHz, CD₃OD): δ 5.65 (m, 2H), 4.7 (m, 1H), 4.44 (m, 1H), 3.48-3.78 (m, 4H), 3.15 (m, 1H), 2.93 (m, 1H), 2.45-2.75 (m, 4H), 1.83 (d, 1H) |

TABLE 2

| STRUCTURE | α6β3β4α5 K$_i$ | Human α4β2 K$_i$ | Rat α4β2 K$_i$ | LCMS (m/z) |
|---|---|---|---|---|
| *N-acetyl diazabicyclic structure* | | 170 | | 141 |
| *N-isobutyryl diazabicyclic structure* | 830 | 220 | 23 | 169 |
| *N-cyclopropylcarbonyl diazabicyclic structure* (Compound A) | 140 | 3.0 | 2.3 | 167 |
| *N-propoxycarbonyl diazabicyclic structure* | | 24 | | 185 |
| *N-isopropoxycarbonyl diazabicyclic structure* | | 130 | | 185 |
| *N-(2-methoxyethoxy)carbonyl diazabicyclic structure* | | 120 | | 201 |
| *N-(2-fluoroethoxy)carbonyl diazabicyclic structure* | | 5.9 | 52 | 189 |

TABLE 2-continued

| STRUCTURE | α6β3β4α5 K$_i$ | Human α4β2 K$_i$ | Rat α4β2 K$_i$ | LCMS (m/z) |
|---|---|---|---|---|
| 5-bromo-furan-2-yl carbonyl diazabicycle | 1800 | 25 | 83 | 273 |
| 4-bromo-furan-2-yl carbonyl diazabicycle | 2700 | 35 | 80 | 273 |
| 3-chloro-furan-2-yl carbonyl diazabicycle | 2400 | 7.9 | 56 | 260 |
| isoxazol-5-yl carbonyl diazabicycle | | 150 | | 194 |
| 3-methoxypropanoyl diazabicycle | | 72 | | 185 |
| 3,3,3-trifluoropropanoyl diazabicycle | 1700 | 11 | 25 | 209 |

TABLE 2-continued

| STRUCTURE | α6β3β4α5 K$_i$ | Human α4β2 K$_i$ | Rat α4β2 K$_i$ | LCMS (m/z) |
|---|---|---|---|---|
|  |  | 270 |  | 197 |
|  |  | 38 | 44 | 227 |
|  |  | 66 | 260 | 273 |
|  |  | 14 | 26 | 181 |
|  |  | 370 |  | 185 |
|  |  | 370 |  | 197 |

TABLE 2-continued

| STRUCTURE | α6β3β4α5 K$_i$ | Human α4β2 K$_i$ | Rat α4β2 K$_i$ | LCMS (m/z) |
|---|---|---|---|---|
| | | 6300 | | 249 |
| | | 69 | 520 | 209 |
| | | 2900 | | 211 |
| | | 3400 | | 212 |
| | | 1900 | | 226 |
| | | 400 | | 197 |

TABLE 2-continued
| STRUCTURE | α6β3β4α5 $K_i$ | Human α4β2 $K_i$ | Rat α4β2 $K_i$ | LCMS (m/z) |
|---|---|---|---|---|
| 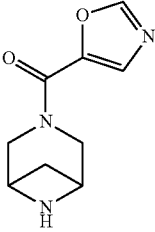 [SMILES: O=C(c1cnco1)N1CC2CC(C1)N2] | 17000 | 28 | 0.18 | 194 |
| 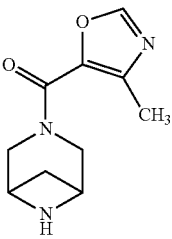 | 11000 | 19 | 38 | 208 |
| 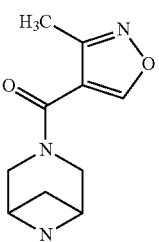 |  | 53 | 60 | 208 |
| 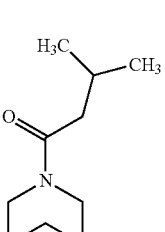 |  | 34 | 70 | 183 |
| 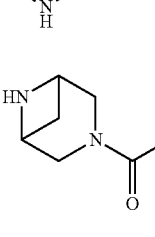 |  | 120 | 390 | 207 |
| 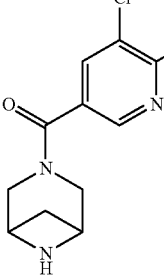 |  | 1500 |  | 272 |

TABLE 2-continued
| STRUCTURE | α6β3β4α5 K$_i$ | Human α4β2 K$_i$ | Rat α4β2 K$_i$ | LCMS (m/z) |
|---|---|---|---|---|
| 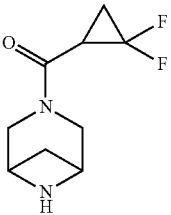 [SMILES: O=C(C1CC1(F)F)N1CC2CC(C1)N2] | 510 | 6.1 | 8.8 | 203 |
| 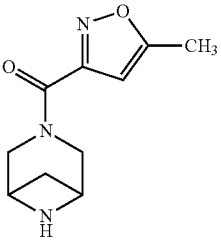 |  | 1100 |  | 208 |
| 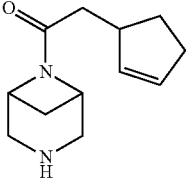 [SMILES: O=C(CC1C=CCC1)N1C2CNCC1C2] |  | 150 | 71 | 207 |
| 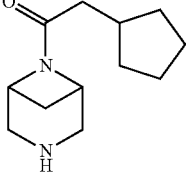 | 360 | 220 | 100 | 209 |
| 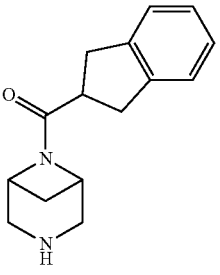 [SMILES: O=C(C1Cc2ccccc2C1)N1C2CNCC1C2] |  | 3000 |  | 243 |
| 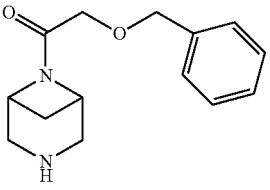 [SMILES: O=C(COCc1ccccc1)N1C2CNCC1C2] |  | 1400 |  | 247 |
| 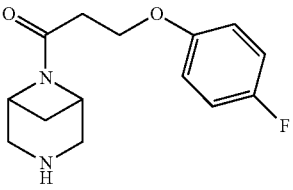 [SMILES: O=C(CCOc1ccc(F)cc1)N1C2CNCC1C2] |  | 1200 |  | 265 |

TABLE 2-continued

| STRUCTURE | α6β3β4α5 K$_i$ | Human α4β2 K$_i$ | Rat α4β2 K$_i$ | LCMS (m/z) |
|---|---|---|---|---|
| | | 9400 | | 229 |
| | | 7100 | | 247 |
| 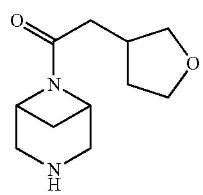 [SMILES: O=C(CC1CCOC1)N1C2CNCC1C2] | 1600 | 330 | 130 | 211 |
| | | 2200 | | 256 |
| | | 1300 | | 251 |
| | | 2000 | | 211 |
| 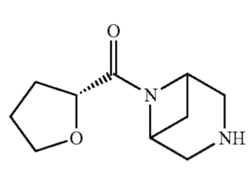 [SMILES: O=C([C@H]1CCCO1)N1C2CNCC1C2] | 1100 | 390 | | 197 |

TABLE 2-continued
| STRUCTURE | α6β3β4α5 K$_i$ | Human α4β2 K$_i$ | Rat α4β2 K$_i$ | LCMS (m/z) |
|---|---|---|---|---|
|  | | 750 | | 197 |
|  | | 3300 | | 225 |
|  | | 2900 | | 256 |
|  | | 2000 | | 211 |
| 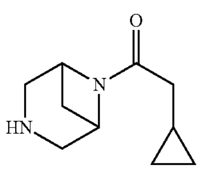 [SMILES: O=C(CC1CC1)N1C2CNCC1C2] | 310 | 43 | 27 | 181 |
| 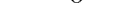 | | 37 | 260 | 193 |
|  | | 79 | 50 | 171 |
|  | | 150 | 240 | 183 |
|  | | 430 | | 182 |

TABLE 2-continued
| STRUCTURE | α6β3β4α5 K$_i$ | Human α4β2 K$_i$ | Rat α4β2 K$_i$ | LCMS (m/z) |
|---|---|---|---|---|
| 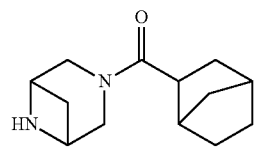 [SMILES: O=C(C1CC2CCC1C2)N1CC2CC(C1)N2] | | 60 | 220 | 221 |
| 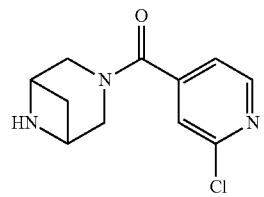 [SMILES: O=C(c1ccnc(Cl)c1)N1CC2CC(C1)N2] | | 450 | | 238 |
| 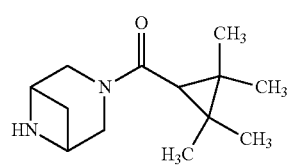 | 480 | 140 | 710 | 223 |
| 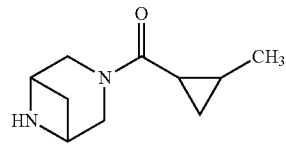 | 120 | 5.0 | 1.8 | 181 |
| 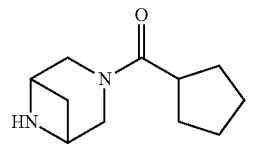 | | 170 | 77 | 195 |
| 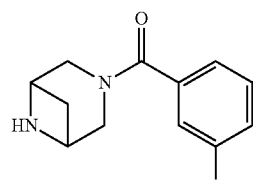 | | 3300 | | 271 |
| 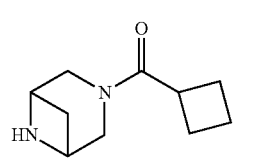 [SMILES: O=C(C1CCC1)N1CC2CC(C1)N2] | | 28 | 6.8 | 181 |
| 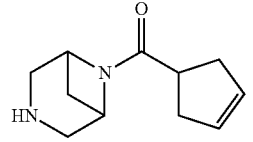 [SMILES: O=C(C1CC=CC1)N1C2CNCC1C2] | | 810 | | 193 |
| 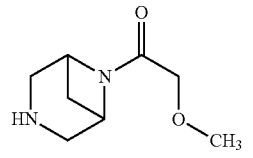 | | 410 | | 171 |

TABLE 2-continued

| STRUCTURE | α6β3β4α5 K$_i$ | Human α4β2 K$_i$ | Rat α4β2 K$_i$ | LCMS (m/z) |
|---|---|---|---|---|
| | | 290 | | 183 |
| | | 1700 | | 221 |
| | | 970 | | 238 |
| | | 11000 | | 223 |
| | | 46 | 34 | 181 |
| | | 420 | | 195 |
| 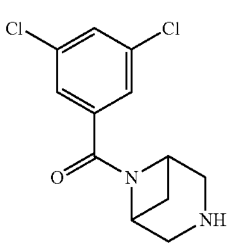 [SMILES: O=C(c1cc(Cl)cc(Cl)c1)N1C2CNCC1C2] | 14000 | 1200 | | 271 |

TABLE 2-continued

| STRUCTURE | α6β3β4α5 K$_i$ | Human α4β2 K$_i$ | Rat α4β2 K$_i$ | LCMS (m/z) |
|---|---|---|---|---|
| 5-methylisoxazol-3-yl carbonyl diazabicycle | | 100 | 50 | 208 |
| 4-methyloxazol-5-yl carbonyl diazabicycle | | 140 | 250 | 208 |
| 3-methylisoxazol-4-yl carbonyl diazabicycle | | 1100 | | 208 |
| oxazol-5-yl carbonyl diazabicycle | | 72 | 17 | 194 |
| isobutyryl diazabicycle | | 260 | | 169 |
| 3-methylbutanoyl diazabicycle | | 120 | 59 | 183 |
| cyclohex-3-enyl carbonyl diazabicycle | | 1200 | | 207 |

TABLE 2-continued

| STRUCTURE | α6β3β4α5 $K_i$ | Human α4β2 $K_i$ | Rat α4β2 $K_i$ | LCMS (m/z) |
|---|---|---|---|---|
| | | 760 | | 209 |
| | | 11 | 34 | 207 |
| | | 440 | | 209 |
| | | 800 | | 243 |
| | | 1000 | | 247 |
| | | 660 | | 265 |
| | | 2000 | | 229 |

TABLE 2-continued
| STRUCTURE | α6β3β4α5 K$_i$ | Human α4β2 K$_i$ | Rat α4β2 K$_i$ | LCMS (m/z) |
|---|---|---|---|---|
| 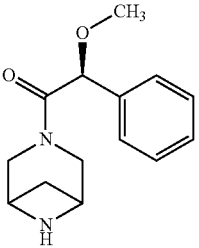 [SMILES: CO[C@H](C(=O)N1CC2CC(C1)N2)c1ccccc1] | | 950 | | 247 |
| 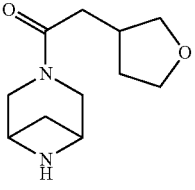 [SMILES: O=C(CC1CCOC1)N1CC2CC(C1)N2] | | 240 | | 211 |
| 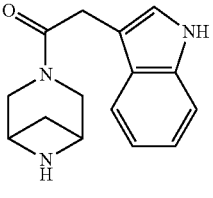 [SMILES: O=C(Cc1c[nH]c2ccccc12)N1CC2CC(C1)N2] | | 750 | | 256 |
| 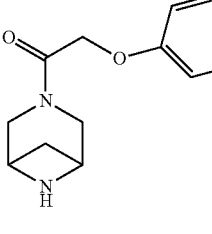 | | 360 | | 251 |
| 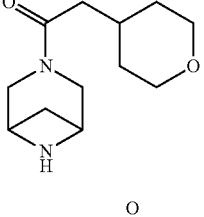 | | 2800 | | 225 |
| 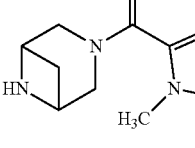 | | 420 | | 256 |
| 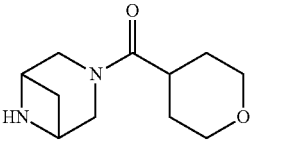 [SMILES: O=C(C1CCOCC1)N1CC2CC(C1)N2] | | 320 | | 211 |
| 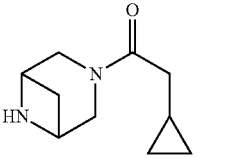 | | 64 | 17 | 181 |

TABLE 2-continued

| STRUCTURE | α6β3β4α5 K$_i$ | Human α4β2 K$_i$ | Rat α4β2 K$_i$ | LCMS (m/z) |
|---|---|---|---|---|
| (cis-fluorocyclopropyl carbonyl diazabicyclic) | 530 | 5.2 | 1.1 | 185 |
| (cis-fluorocyclopropyl carbonyl diazabicyclic, other stereoisomer) | 120 | 4.5 | 0.81 | 185 |
| (fluorocyclopropyl carbonyl diazabicyclic) | | 3.7 | 0.89 | 185 |
| (fluorocyclopropyl carbonyl diazabicyclic, stereoisomer) | | 2.2 | 1.0 | 185 |
| (3,4-dichlorophenylthio acetyl diazabicyclic) | 100 | 2.3 | 16 | 318 |
| (4-hydroxyphenylthio acetyl diazabicyclic) | 120 | 11 | 8.6 | 265 |
| (3,4-dichlorophenoxy acetyl diazabicyclic) | 700 | 330 | | 302 |
| (4-chlorobenzyl urea diazabicyclic) | 3400 | 6500 | | 267 |
| (2,4-dichlorobenzyl urea diazabicyclic) | 21000 | 1100 | | 301 |

TABLE 2-continued
| STRUCTURE | α6β3β4α5 K$_i$ | Human α4β2 K$_i$ | Rat α4β2 K$_i$ | LCMS (m/z) |
|---|---|---|---|---|
| 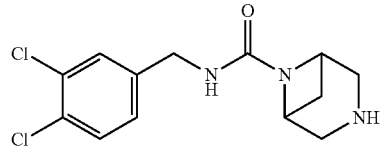 [SMILES: O=C(NCc1ccc(Cl)c(Cl)c1)N1C2CNCC1C2] | 5900 | 3100 | | 301 |
| 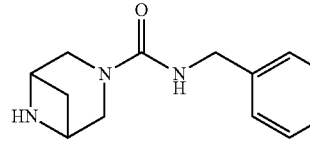 | 400 | 270 | 200 | 232 |
| 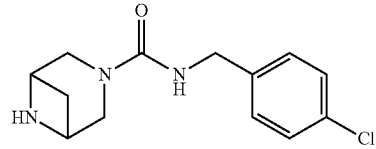 [SMILES: O=C(NCc1ccc(Cl)cc1)N1CC2CC(C1)N2] | 210 | 110 | 4.0 | 267 |
| 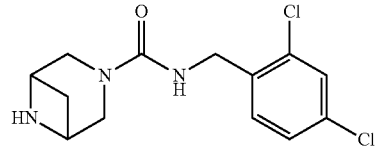 | 38 | 48 | 24 | 301 |
| 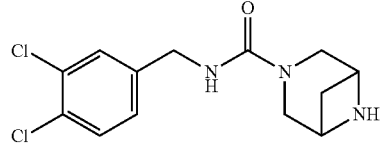 [SMILES: O=C(NCc1ccc(Cl)c(Cl)c1)N1CC2CC(C1)N2] | 120 | 90 | 71 | 301 |
| 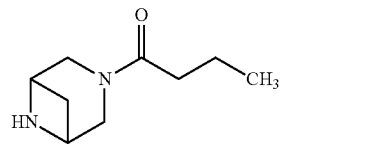 | 290 | 12 | 4.1 | 169 |
| 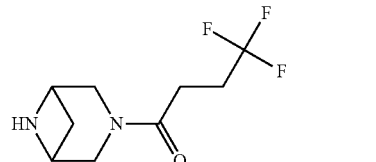 | 980 | 74 | 63 | 223 |
| 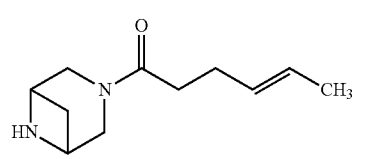 | 540 | 37 | 25 | 195 |
| 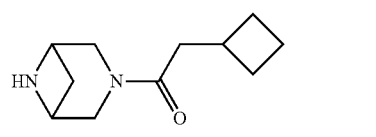 | 440 | 49 | 34 | 195 |
| 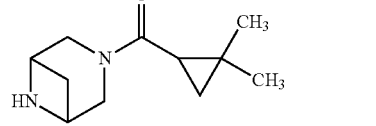 | 120 | 5.3 | 6.7 | 195 |

TABLE 2-continued

| STRUCTURE | α6β3β4α5 K$_i$ | Human α4β2 K$_i$ | Rat α4β2 K$_i$ | LCMS (m/z) |
|---|---|---|---|---|
| 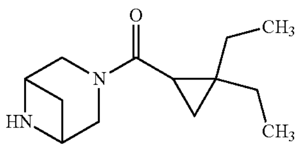 [SMILES: CCC1(CC)CC1C(=O)N1CC2CC(C1)N2] | 470 | 71 | 69 | 223 |
| 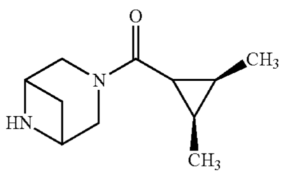 | 170 | 44 | 30 | 195 |
| 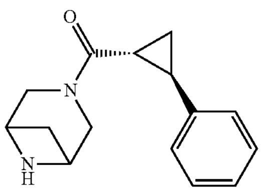 [SMILES: O=C([C@@H]1C[C@H]1c1ccccc1)N1CC2CC(C1)N2] | 64 | 4.7 | 4.4 | 243 |
| 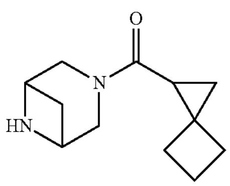 [SMILES: O=C(C1CC12CCC2)N1CC2CC(C1)N2] | 50 | 2.6 | 1.2 | 207 |
| 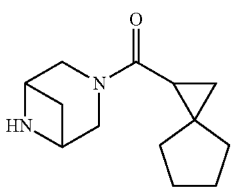 [SMILES: O=C(C1CC12CCCC2)N1CC2CC(C1)N2] | 96 | 26 | 31 | 221 |
| 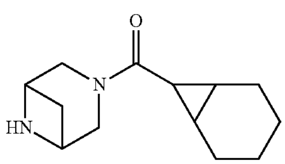 [SMILES: O=C(C1C2CCCCC21)N1CC2CC(C1)N2] | 280 | 78 | 30 | 221 |
| 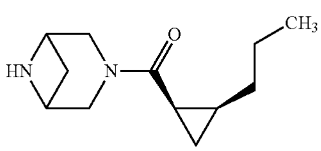 | 220 | 44 | 130 | 209 |
| 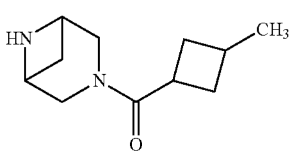 | 380 | 23 | 22 | 195 |
| 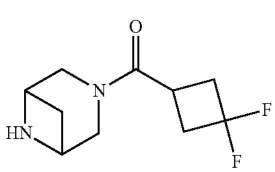 [SMILES: O=C(C1CC(F)(F)C1)N1CC2CC(C1)N2] | 370 | 16 | 19 | 217 |

TABLE 2-continued
| STRUCTURE | α6β3β4α5 $K_i$ | Human α4β2 $K_i$ | Rat α4β2 $K_i$ | LCMS (m/z) |
|---|---|---|---|---|
| 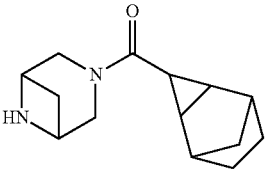 [SMILES: O=C(C1C2C3CCC(C3)C12)N1CC2CC(C1)N2] | 22000 | 1300 | | 233 |
| 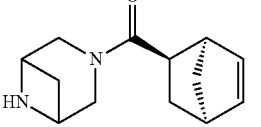 | 1300 | 160 | 210 | 219 |
| 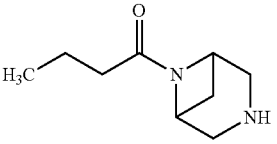 | 230 | 9.9 | 5.1 | 169 |
| 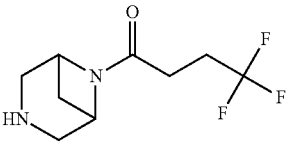 [SMILES: O=C(CCC(F)(F)F)N1C2CNCC1C2] | 1500 | 180 | 72 | 223 |
| 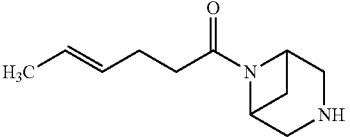 | 400 | 53 | 15 | 195 |
| 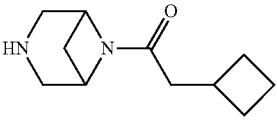 [SMILES: O=C(CC1CCC1)N1C2CNCC1C2] | 360 | 53 | 30 | 195 |
| 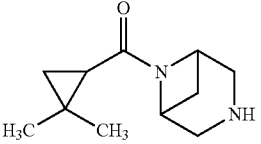 | 800 | 75 | 45 | 195 |
| 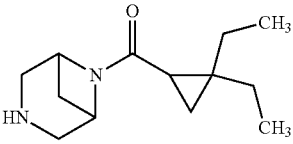 [SMILES: CCC1(CC)CC1C(=O)N1C2CNCC1C2] | 4400 | 850 | | 223 |
| 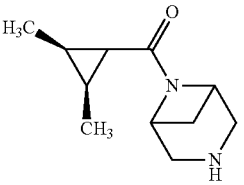 | 2400 | 610 | | 195 |

TABLE 2-continued

| STRUCTURE | α6β3β4α5 K$_i$ | Human α4β2 K$_i$ | Rat α4β2 K$_i$ | LCMS (m/z) |
|---|---|---|---|---|
| 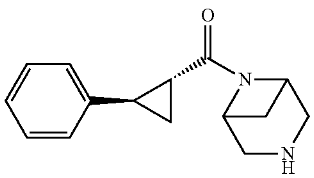 [SMILES: O=C([C@@H]1C[C@H]1c1ccccc1)N1C2CNCC1C2] | 350 | 30 | 51 | 243 |
| 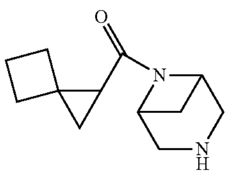 [SMILES: O=C(C1CC12CCC2)N1C2CNCC1C2] | 340 | 38 | 32 | 207 |
| 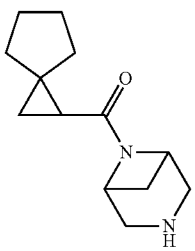 [SMILES: O=C(C1CC12CCCC2)N1C2CNCC1C2] | 610 | 280 | | 221 |
| 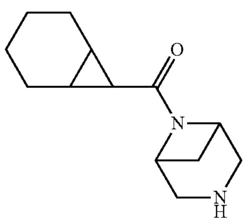 [SMILES: O=C(C1C2CCCCC21)N1C2CNCC1C2] | 6400 | 310 | | 221 |
| 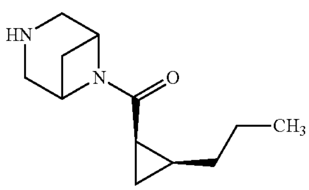 | 1100 | 570 | | 209 |
| 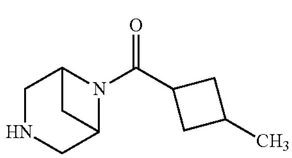 | 770 | 49 | 58 | 195 |
| 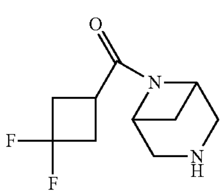 [SMILES: O=C(C1CC(F)(F)C1)N1C2CNCC1C2] | 510 | 54 | 16 | 217 |
| 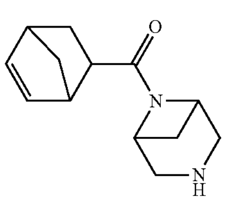 [SMILES: O=C(C1CC2C=CC1C2)N1C2CNCC1C2] | 900 | 200 | 380 | 219 |

TABLE 2-continued

| STRUCTURE | α6β3β4α5 $K_i$ | Human α4β2 $K_i$ | Rat α4β2 $K_i$ | LCMS (m/z) |
|---|---|---|---|---|
| 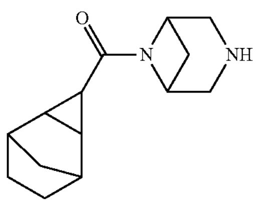 [SMILES: O=C(C1C2C3CCC(C3)C12)N1C2CNCC1C2] | 100000 | 1900 | | 233 |
| 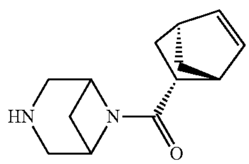 [SMILES: O=C([C@@H]1C[C@H]2C=C[C@H]1C2)N1C2CNCC1C2] | 1300 | 300 | | 219 |
| 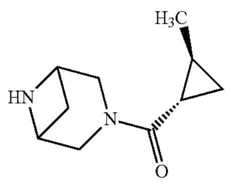 | 2600 | 7.6 | 100 | 181 |
| 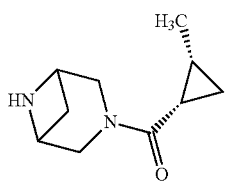 | 1100 | 22 | 200 | 181 |
| 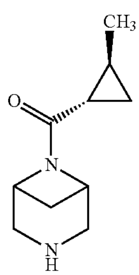 | 31000 | 210 | | 181 |
| 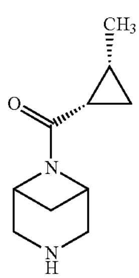 | 30000 | 820 | | 181 |
| 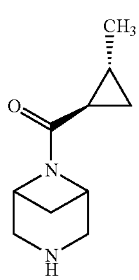 | 1700 | 9.2 | 50 | 181 |

TABLE 2-continued
| STRUCTURE | α6β3β4α5 K$_i$ | Human α4β2 K$_i$ | Rat α4β2 K$_i$ | LCMS (m/z) |
|---|---|---|---|---|
| 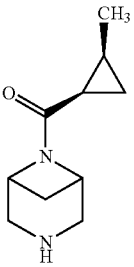 | 1800 | 9.6 | 180 | 181 |
| 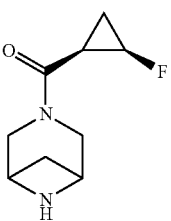 [SMILES: O=C([C@H]1C[C@H]1F)N1CC2CC(C1)N2] | 150 | 1.1 | 0.53 | 185 |
| 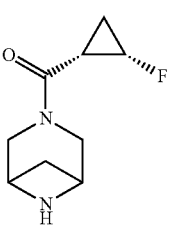 [SMILES: O=C([C@@H]1C[C@@H]1F)N1CC2CC(C1)N2] | 280 | 1.8 | 0.86 | 185 |
| 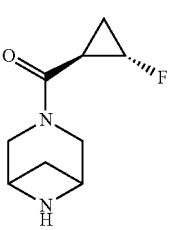 [SMILES: O=C([C@H]1C[C@@H]1F)N1CC2CC(C1)N2] | 780 | 4.6 | 1.6 | 185 |
| 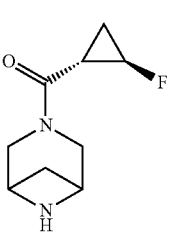 [SMILES: O=C([C@@H]1C[C@H]1F)N1CC2CC(C1)N2] | 91 | 1 | 0.54 | 185 |
| 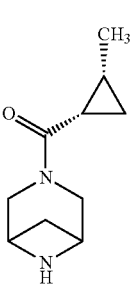 | 830 | 22 | 4 | 181 |

TABLE 2-continued

| STRUCTURE | α6β3β4α5 K$_i$ | Human α4β2 K$_i$ | Rat α4β2 K$_i$ | LCMS (m/z) |
|---|---|---|---|---|
| (cyclopropyl-CH₃ carbonyl-diazabicyclic) | 58 | 1.8 | 0.39 | 181 |
| (cyclopropyl-CH₃ carbonyl-diazabicyclic, stereoisomer) | 95 | 1 | 0.08 | 181 |
| (cyclopropyl-CH₃ carbonyl-diazabicyclic, stereoisomer) | 1700 | 13 | 4.8 | 181 |
| (deuterated cyclopropyl carbonyl-diazabicyclic) | 120 | 0.49 | 0.24 | 143 |

Compounds of Table 2, representative of the present invention, exhibited inhibition constants (Ki values) at the human α4β2 subtype in the ranges of 2 nM to 11,000 nM, with a number of compound exhibiting Ki<100 nM, indicating high affinity for the α4β2 subtype. Ki values at the α6β3β4α5 subtype vary within the range of 38 nM to 100,000 nM, indicating variable affinity for the α6β3β4α5 subtype.

Example 11

Neuroprotective Effect of 48 h Pre-Treatment of Dopaminergic Neurons with Test Compounds on MPP⁺ Injuries (4 μM)

Experimental Protocol
Primary Cultures of Dopaminergic Neurons

Rat dopaminergic neurons were cultured as described by Schinelli et al., 1988. Briefly pregnant female rats of 15 days gestation were killed by cervical dislocation (Rats Wistar; Janvier) and the fetuses removed from the uterus. The embryonic midbrains were removed and placed in ice-cold medium of Leibovitz (L15; Invitrogen) containing 1% of Penicillin-Streptomycin (PS; Invitrogen) and 1% of bovine serum albumin (BSA; Sigma). Only the ventral portions of the mesencephalic flexure were used for the cell preparations as this is the region of the developing brain rich in dopaminergic neurons. The midbrains were dissociated by trypsinisation for 20 min at 37° C. (Trypsin EDTA 1×; Invitrogen) diluted in PBS without calcium and magnesium. The reaction was stopped by the addition of Dulbecco's modified Eagle's medium (DMEM; Invitrogen) containing DNAase I grade II (0.1 mg/ml; Roche Diagnostic) and 10% of foetal calf serum (FCS; Invitrogen). Cells were then mechanically dissociated by 3 passages through a 10 ml pipette. Cells were then centrifuged at 180×g for 10 min at room temperature on a layer of BSA (3.5%) in L15 medium. The supernatant was discarded and the cells of pellet were re-suspended in a defined culture medium consisting of Neurobasal (Invitrogen) supplemented with B27 (2%; Invitrogen), L-glutamine (0.2 mM; Invitrogen) and 1% of PS solution. Viable cells were counted in a Neubauer cytometer using the trypan blue exclusion test. The cells were seeded at a density of 35000 cells/well in 96 well-plates (wells were pre-coated with poly-L-lysine (greiner)) and were cultured at 37° C. in a humidified air (95%)/CO2 (5%) atmosphere. Half of the medium was changed every 2 days with fresh medium. In these conditions, after 5 days of culture, astrocytes were present in the culture and release growth factor allowing neurons differentiation. Five to six percents of the neuronal cell population were dopaminergic neurons.

Drug Treatments and Dopaminergic Neuron Immunostaining Methods

Briefly, on day 3 of culture, the medium was removed and fresh medium with or without test compounds, nicotine (10 nM) or BDNF (Brain Derived Neurotropic Factor, 50 ng/ml) was added for a 48 h pre-incubation. On day 5 MPP$^+$ at 4 µM was added (in presence of test compounds, nicotine or BDNF), 6 wells per condition were done.

After 48 h of MPP$^+$ intoxication with or without test compounds, nicotine (10 nM) or BDNF (50 ng/ml), cells were fixed (all conditions) by paraformaldehyde 4% solution Test compounds (compound A and compound B, as the heptane di-p-toluoyl-D-tartrate salts) were assayed at seven concentrations (0.001; 0.01; 0.1; 1; 10; 100 and 1000 nM).

Nicotine (10 nM) and BDNF (50 ng/ml) were used as reference test compounds.

After permeabilization with 0.1% saponin (Sigma), cells were incubated with mouse monoclonal primary against tyrosine hydroxylase antibody (TH, Sigma) for dopaminergic neurons The total neurite were measured in parallel on same wells.

This antibody was revealed with Alexa Fluor 488 goat anti-mouse IgG (Molecular probe).

Analysis and Method of Quantification

For each condition, 20 pictures per well were taken in the same condition using InCell Analyzer™ 1000 (GE Healthcare) with 10× magnification. The analyses were automatically done using developer software (GE Healthcare) to measure the total number of TH positive neurons and the total neurite length. Data were expressed in percentage of control condition.

Statistical analyses (using Statview package) were done on the different conditions using ANOVA test following by Dunnett's test (when allowed), significance was set for $p \leq 0.05$.

The results are illustrated in FIGS. 1-6.

FIG. 1 shows a dose effect curve of Compound A (3-cyclopropylcarbonyl-3,6-diazabicyclo[3.1.1], as the heptane di-p-toluoyl-D-tartrate salt) and nicotine on TH positive neurons after 48 h pretreatment, followed by MPP$^+$ injury (4 µM, 48 h).

Figure 2:
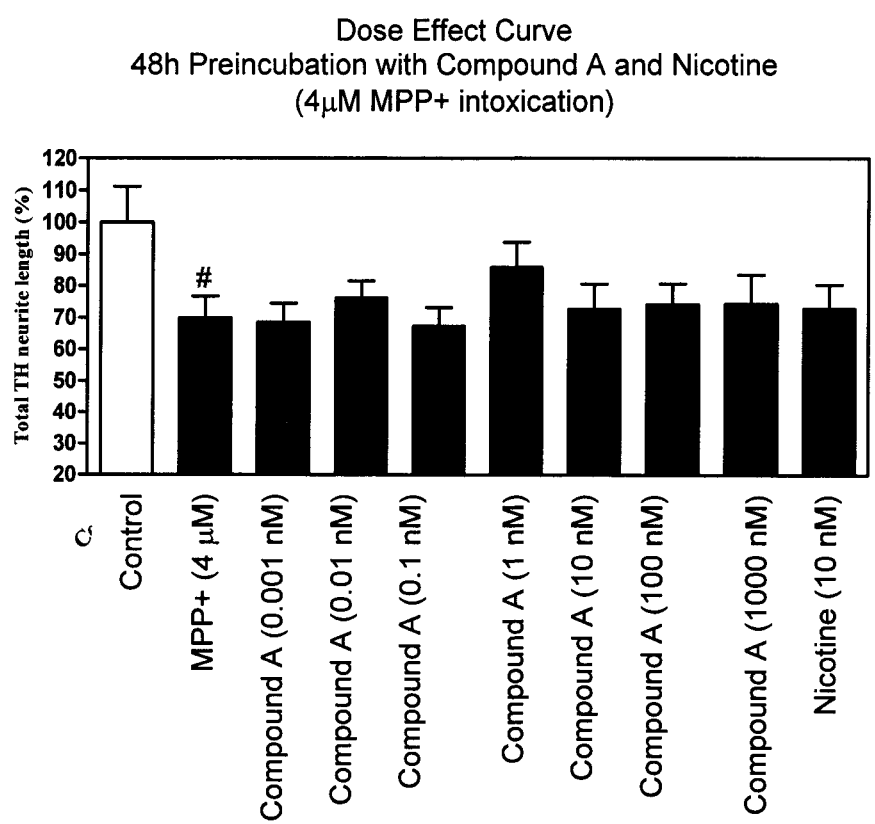
FIG. 2 illustrates a dose effect curve of Compound A (3-cyclopropylcarbonyl-3,6-diazabicyclo[3.1.1], as the heptane di-p-toluoyl-D-tartrate salt) and nicotine on total TH neurite length after 48 h pretreatment, followed by MPP$^+$ injury (4 μM, 48 h).

FIG. 2 shows a dose effect curve of Compound A (3-cyclopropylcarbonyl-3,6-diazabicyclo[3.1.1], as the heptane di-p-toluoyl-D-tartrate salt) and nicotine on total TH neurite length after 48 h pretreatment, followed by MPP$^+$ injury (4 µM, 48 h).

Figure 3:
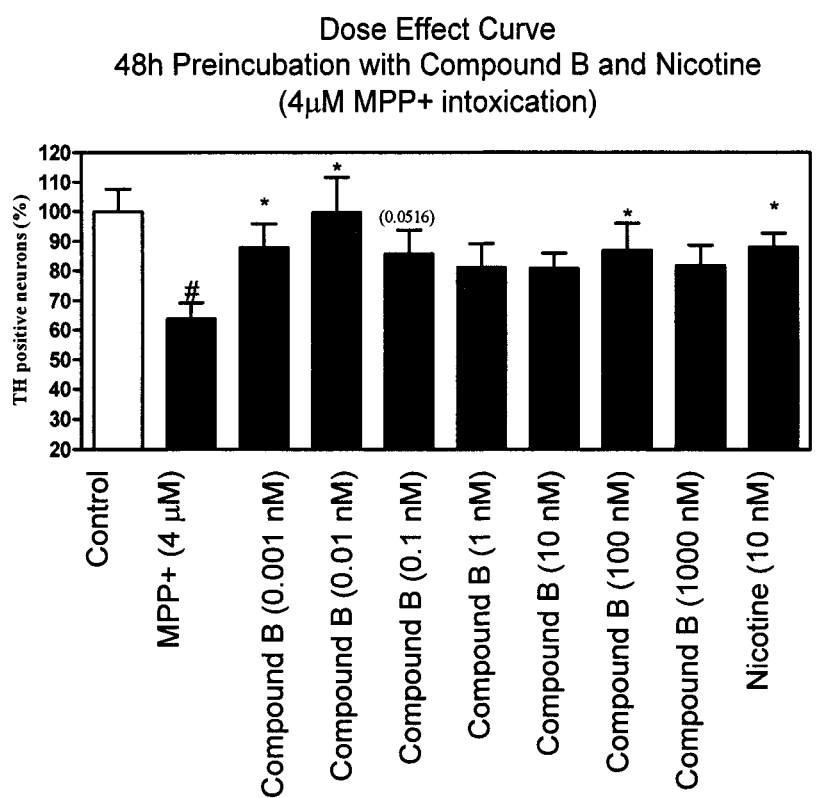
FIG. 3 illustrates a dose effect curve of Compound B (3-ethylcarbonyl-3,6-diazabicyclo[3.1.1], as the heptane di-p-toluoyl-D-tartrate salt) and nicotine on TH positive neurons after 48 h pretreatment, followed by MPP$^+$ injury (4 μM, 48 h).

FIG. 3 shows a dose effect curve of Compound B (3-ethylcarbonyl-3,6-diazabicyclo[3.1.1], as the heptane di-p-toluoyl-D-tartrate salt) and nicotine on TH positive neurons after 48 h pretreatment, followed by MPP$^+$ injury (4 µM, 48 h).

Figure 4:
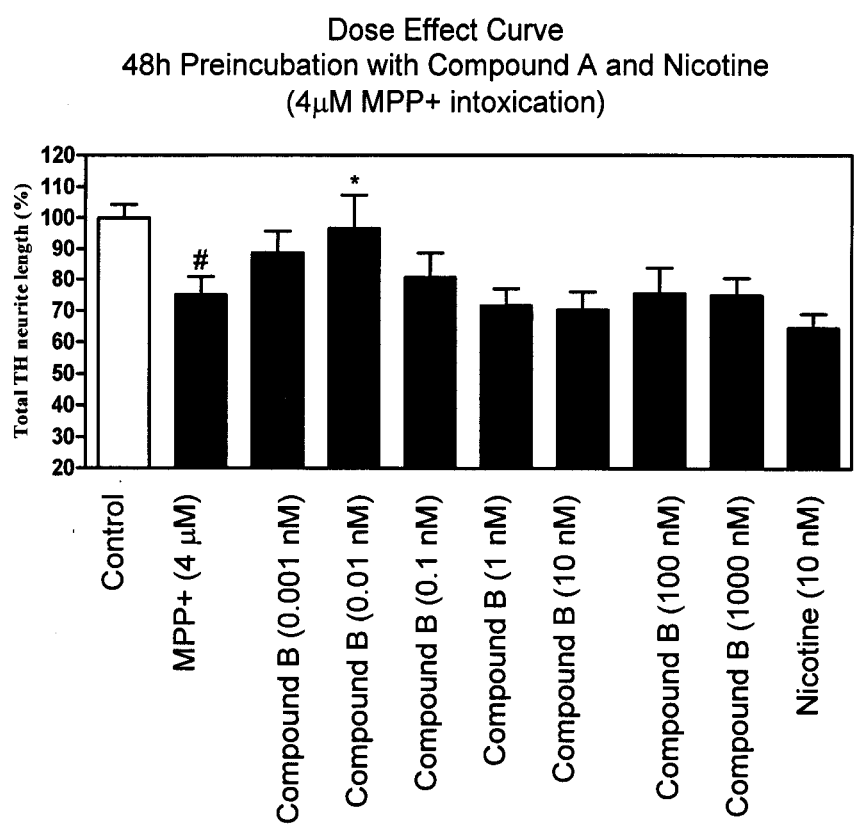
FIG. 4 illustrates a dose effect curve of Compound B (3-ethylcarbonyl-3,6-diazabicyclo[3.1.1], as the heptane dip-toluoyl-D-tartrate salt) and nicotine on total TH neurite length after 48 h pretreatment, followed by MPP+ injury (4 μM, 48 h).

FIG. 4 shows a dose effect curve of Compound B (3-ethylcarbonyl-3,6-diazabicyclo[3.1.1], as the heptane di-p-toluoyl-D-tartrate salt) and nicotine on total TH neurite length after 48 h pretreatment, followed by MPP$^+$ injury (4 µM, 48 h).

Figure 5:
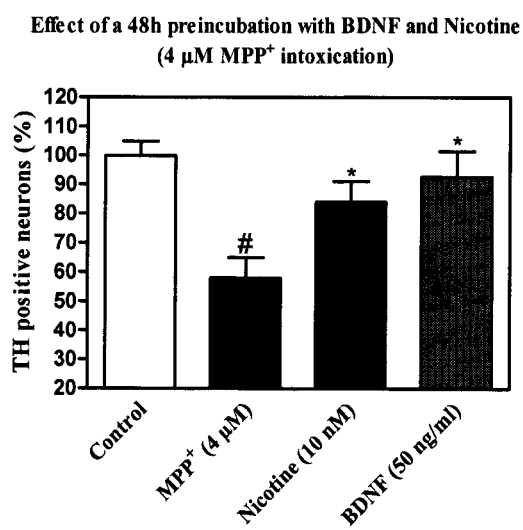
FIG. 5 illustrates a dose effect curve of BDNF (50 ng/ml) and nicotine (10 nM) on TH positive neurons after 48 h pretreatment, followed by MPP+ injury (4 μM, 48 h).

FIG. 5 shows a dose effect curve of BDNF (50 ng/ml) and nicotine (10 nM) on TH positive neurons after 48 h pretreatment, followed by MPP$^+$ injury (4 µM, 48 h).

Figure 6:
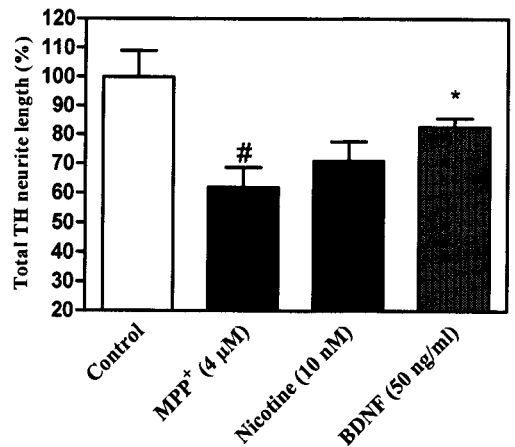
FIG. 6 illustrates a dose effect curve of BDNF (50 ng/ml) and nicotine (10 nM) on total TH neurite length after 48 h pretreatment, followed by MPP+ injury (4 μM, 48 h).

FIG. 6 shows a dose effect curve of BDNF (50 ng/ml) and nicotine (10 nM) on total TH neurite length after 48 h pretreatment, followed by MPP$^+$ injury (4 µM, 48 h).

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound selected from:
   3-methylcarbonyl-3,6-diazabicyclo[3.1.1]heptane;
   3-isopropylcarbonyl-3,6-diazabicyclo[3.1.1]heptane;
   3-cyclopropylcarbonyl-3,6-diazabicyclo[3.1.1]heptane;
   3-propoxycarbonyl-3,6-diazabicyclo[3.1.1]heptane;
   3-isopropoxycarbonyl-3,6-diazabicyclo[3.1.1]heptanes;
   3-methoxyethoxycarbonyl-3,6-diazabicyclo[3.1.1]heptane;
   3-(2-fluoroethoxy)carbonyl-3,6-diazabicyclo[3.1.1]heptane;
   3-(2-bromofuran-5-yl)carbonyl-3,6-diazabicyclo[3.1.1]heptane;
   3-(3-bromofuran-5-yl)carbonyl-3,6-diazabicyclo[3.1.1]heptane;
   3-(3-chlorofuran-2-yl)carbonyl-3,6-diazabicyclo[3.1.1]heptane;
   3-(isoxazol-5-yl)carbonyl-3,6-diazabicyclo[3.1.1]heptane;
   3-(2-methoxyethyl)carbonyl-3,6-diazabicyclo[3.1.1]heptane;
   3-(2,2,2-trifluoroethyl)carbonyl-3,6-diazabicyclo[3.1.1]heptane;
   3-(tetrahydrofuran-3-yl)carbonyl-3,6-diazabicyclo[3.1.1]heptane;
   6-(2-chlorofuran-5-yl)carbonyl-3,6-diazabicyclo[3.1.1]heptane;
   6-(2-bromorofuran-5-yl)carbonyl-3,6-diazabicyclo[3.1.1]heptane;
   6-cyclobutylcarbonyl-3,6-diazabicyclo[3.1.1]heptane;
   6-(2-methoxyethyl)carbonyl-3,6-diazabicyclo[3.1.1]heptane;
   cis-3-(2-fluorocycloprop-1-yl)carbonyl-3,6-diazabicyclo[3.1.1]heptane;
   trans-3-(2-fluorocycloprop-1-yl)carbonyl-3,6-diazabicyclo[3.1.1]heptane;
   cis-6-(2-fluorocycloprop-1-yl)carbonyl-3,6-diazabicyclo[3.1.1]heptane; and
   trans-6-(2-fluorocycloprop-1-yl)carbonyl-3,6-diazabicyclo[3.1.1]heptane;
   or a pharmaceutically acceptable salt thereof.

2. A compound 3-cyclopropylcarbonyl-3,6-diazabicyclo[3.1.1]heptane or a pharmaceutically acceptable salt thereof.

3. A pharmaceutical composition comprising a compound as claimed in claim 1 and a pharmaceutically acceptable carrier.

4. A pharmaceutical composition comprising a compound as claimed in claim 2 and a pharmaceutically acceptable carrier.

5. The pharmaceutical composition of claim 3, wherein the composition is formulated for intranasal, buccal, or sublingual administration.

6. The pharmaceutical composition of claim 4, wherein the composition is formulated for intranasal, buccal, or sublingual administration.

* * * * *